United States Patent
Magome et al.

(10) Patent No.: US 9,446,137 B2
(45) Date of Patent: *Sep. 20, 2016

(54) COMPOSITE PARTICLES WHICH CONTAIN BOTH CELLULOSE AND INORGANIC COMPOUND

(71) Applicant: ASAHI KASEI CHEMICALS CORPORATION, Tokyo (JP)

(72) Inventors: Takumi Magome, Tokyo (JP); Kazuhiro Obae, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/591,514

(22) Filed: Jan. 7, 2015

(65) Prior Publication Data

US 2015/0174255 A1 Jun. 25, 2015

Related U.S. Application Data

(63) Continuation of application No. 13/807,373, filed as application No. PCT/JP2011/064420 on Jun. 23, 2011, now Pat. No. 8,951,636.

(30) Foreign Application Priority Data

Jun. 29, 2010 (JP) .................................. 2010-147663

(51) Int. Cl.
*B32B 5/16* (2006.01)
*B32B 5/18* (2006.01)
(Continued)

(52) U.S. Cl.
CPC .................. *A61K 47/38* (2013.01); *A23L 1/00* (2013.01); *A23L 1/002* (2013.01); *A23L 1/304* (2013.01); *A61K 9/14* (2013.01); *A61K 9/2054* (2013.01);
(Continued)

(58) Field of Classification Search
CPC .......................................... C08L 1/02
USPC .................. 428/402, 308.4, 319.1, 407, 532
See application file for complete search history.

(56) References Cited

U.S. PATENT DOCUMENTS

| 4,744,987 A | 5/1988 | Mehra et al. |
| 5,585,115 A | 12/1996 | Sherwood et al. |

(Continued)

FOREIGN PATENT DOCUMENTS

| JP | 63-267731 | * 11/1988 | ............. A61K 47/00 |
| JP | 3-52823 | 3/1991 | |

(Continued)

OTHER PUBLICATIONS

DL-alpha Tocopheryl Acetate—Kyowa Hakko Europe GmbH (1990).*

(Continued)

*Primary Examiner* — Holly Le
(74) *Attorney, Agent, or Firm* — Greenblum & Bernstein, P.L.C.

(57) ABSTRACT

Provided are composite particles which exhibit excellent fluidity and high liquid retentivity and which exhibit high fluidity even in a liquid-holding state. Also provided are composite particles which permit direct compressing in an open feed manner and which suffer from little compressing trouble and exhibit high shapability. When shaped together with an active ingredient, the composite particles provide shaped bodies which have uniform weight, uniform active ingredient content, and high hardness and which suffer from less galling.

12 Claims, 3 Drawing Sheets

(51) Int. Cl.
  *A61K 47/38* (2006.01)
  *C08J 3/12* (2006.01)
  *C08L 1/02* (2006.01)
  *A61K 47/02* (2006.01)
  *A61K 31/355* (2006.01)
  *C08K 3/34* (2006.01)
  *A23L 1/304* (2006.01)
  *A61K 9/14* (2006.01)
  *A61K 47/36* (2006.01)
  *A61K 9/20* (2006.01)
  *A23L 1/00* (2006.01)

(52) U.S. Cl.
  CPC ............ *A61K 31/355* (2013.01); *A61K 47/02* (2013.01); *A61K 47/36* (2013.01); *C08J 3/122* (2013.01); *C08K 3/34* (2013.01); *C08L 1/02* (2013.01); *A23L 1/0035* (2013.01); *A23V 2002/00* (2013.01); *A61K 9/2009* (2013.01); *C08J 2301/02* (2013.01); *Y10T 428/24999* (2015.04); *Y10T 428/249958* (2015.04); *Y10T 428/2982* (2015.01); *Y10T 428/2991* (2015.01); *Y10T 428/2998* (2015.01); *Y10T 428/31971* (2015.04)

(56) References Cited

U.S. PATENT DOCUMENTS

| | | | |
|---|---|---|---|
| 5,725,883 | A | 3/1998 | Staniforth et al. |
| 5,725,884 | A | 3/1998 | Sherwood et al. |
| 5,858,412 | A | 1/1999 | Staniforth et al. |
| 5,948,438 | A | 9/1999 | Staniforth et al. |
| 6,103,219 | A | 8/2000 | Sherwood et al. |
| 6,358,533 | B2 | 3/2002 | Sherwood et al. |
| 6,521,261 | B2 | 2/2003 | Sherwood et al. |
| 6,858,231 | B2 | 2/2005 | Sherwood et al. |
| 7,514,552 | B2 | 4/2009 | Yamasaki et al. |
| 8,221,789 | B2 | 7/2012 | Obae et al. |
| 8,951,636 | B2 * | 2/2015 | Magome et al. ............ 428/402 |
| 2004/0053887 | A1 | 3/2004 | Obae et al. |
| 2007/0028801 | A1 | 2/2007 | Yamasaki et al. |
| 2009/0022791 | A1 | 1/2009 | Obae et al. |
| 2010/0045636 | A1 | 2/2010 | Noguchi et al. |
| 2010/0291161 | A1 | 11/2010 | Obae et al. |
| 2011/0062630 | A1 | 3/2011 | Honda et al. |
| 2011/0064805 | A1 | 3/2011 | Obae et al. |

FOREIGN PATENT DOCUMENTS

| | | |
|---|---|---|
| JP | 10-500426 | 1/1998 |
| JP | 2001-316248 | 11/2001 |
| JP | 2005-232260 | 9/2005 |
| JP | 2009-137892 | 6/2009 |
| WO | 02/02643 | 1/2002 |
| WO | 2004/106416 | 12/2004 |
| WO | 2006/115198 | 11/2006 |
| WO | 2009/142255 | 11/2009 |

OTHER PUBLICATIONS

Search report from International Application No. PCT/JP2011/064420, mail date is Aug. 30, 2011.

* cited by examiner

COMPOSITE PARTICLES WHICH CONTAIN BOTH CELLULOSE AND INORGANIC COMPOUND

CROSS REFERENCE TO RELATED APPLICATIONS

This application is a Continuation of application Ser. No. 13/807,373 filed Jun. 23, 2011 now U.S. Pat. No. 8,951,636, which is a National Stage of International Application No. PCT/JP2011/064420, filed Jun. 23, 2011, which claims priority to Japanese Application No. 2010-147663, filed Jun. 29, 2010. The disclosures of application Ser. No. 13/807,373 and PCT/JP2011/064420 are expressly incorporated by reference herein in their entirety.

TECHNICAL FIELD

The present invention relates to composite particles having high fluidity and liquid carrying properties, and keeping compactibility and fluidity of the particles even after retention of the liquid to prevent tableting problems.

BACKGROUND ART

Conventionally, in the fields of pharmaceuticals, foods, and other chemical industries, cellulose powder is widely used as an excipient for molding when a molded article containing an active ingredient is prepared. In addition, in the case where the active ingredient is a liquid ingredient, the liquid ingredient is carried by a single inorganic compound to obtain a powder. The obtained powder is molded into a molded article by using a cellulose powder as an excipient.

Unfortunately, the single inorganic compound has an excessively large apparent specific volume, which limits the amount of the active ingredient to be powdered at one time. There is also a handling problem such that the inorganic compound scatters, or the like. For this reason, use of cellulose-inorganic compound porous composite particles as the excipient has been examined.

Patent Literature 1 describes an invention of fine particles produced by co-processing a microcrystalline cellulose particle and calcium carbonate having a particle size less than 30 μm in a specific mass ratio in order to reduce cost of a pharmaceutical excipient.

Patent Literature 2 describes an invention of an excipient composition composed of a fine particle agglomerates including a microcrystalline cellulose and silicon dioxide as a pharmaceutical excipient having improved compressibility.

Patent Literature 3 describes an invention of cellulose inorganic compound porous composite particles which are an aggregate of a specific cellulose dispersed particle and a water-insoluble inorganic compound particle, and having an intraparticle pore volume of 0.260 cm$^3$/g or more. According to Patent Literature 3, the cellulose and the inorganic compound are formed into composite particles to obtain a particle having a large intraparticle pore volume, and high compactibility, disintegration properties, and fluidity.

Patent Literature 4 describes an invention of a solid formulation which is not a composite product but a physical mixture of an inorganic compound and a microcrystalline cellulose, and comprises a drug, calcium silicate, and starch and/or microcrystalline cellulose, in which 10 to 45% by weight of calcium silicate is blended based on the drug, and 40 to 250% by weight of starch and/or microcrystalline cellulose is blended based on calcium silicate. According to the description, even if a drug having poor compactibility such as phenacetin and acetaminophen is directly tableted, 70 to 90 parts by weight of the drug can be blended without capping.

CITATION LIST

Patent Literature

Patent Literature 1: U.S. Pat. No. 4,744,987
Patent Literature 2: JP 10-500426 A
Patent Literature 3: JP 2005-232260 A
Patent Literature 4: JP 3-52823 A

SUMMARY OF INVENTION

Technical Problem

Usually, a tablet is produced by tableting by filling a powder into a die and compressing the powder with a punch. In the case where the drug easily adheres to the punch, it causes a phenomenon called sticking such that the surface of the molded article is peeled off. Usually, a single inorganic compound is used as an excipient, but the single inorganic compound cannot always prevent the sticking. Moreover, because the single inorganic compound has a large apparent specific volume, flushing properties of the powder are increased in tableting to reduce filling properties into the die, leading to problems such as variation in the weight of the molded article and a phenomenon called capping: part of the molded article is peeled off. For this reason, a large amount of the inorganic compound cannot be added.

Cellulose powder is an excipient having high compactibility. Once the cellulose powder gets wet, however, the compactibility is reduced, the function as the excipient is no longer demonstrated. Moreover, compared to the inorganic compound, the cellulose powder has lower liquid retention. Moreover, the composite products of cellulose and an inorganic compound known in the related art have a low liquid retention rate, and low fluidity of the particle after retention of the liquid. In addition, problems such as sticking and capping cannot be sufficiently eliminated.

An object of the present invention is to provide composite particles having a high liquid retention rate and having high fluidity of the particles even after retention of a liquid. In addition, another object of the present invention is to provide composite particles that can be tableted with gravity feeder in a direct tableting method, hardly cause tableting problems, and have high compactibility. Further another object of the present invention is to provide a molded article in which the weight of the molded article and the content of an active ingredient are uniform, hardness is high, and friability is low when the composite particles and the active ingredient are formed into the molded article.

Solution to Problem

In order to solve the problems above, the present inventors have found out that if cellulose and an inorganic compound are formed into a composite product, the apparent specific volume, the pore volume, and the liquid retention rate can be increased, and compactibility and fluidity of the particles even after retention of a liquid can be increased. Thus, the present invention has been made.

Namely, the present invention is as follows.
(1) Composite particles comprising a cellulose and an inorganic compound, and having an apparent specific volume of 7 to 13 cm$^3$/g.
(2) The composite particles according to (1), wherein the cellulose has an average width of 2 to 30 μm and an average thickness of 0.5 to 5 μm.
(3) The composite particles according to (1) or (2), comprising 10 to 60 parts by mass of the cellulose and 40 to 90 parts by mass of the inorganic compound.
(4) The composite particles according to any one of (1) to (3), wherein the inorganic compound is at least one selected from the group consisting of silicon dioxide hydrate, light anhydrous silicic acid, synthetic aluminum silicate, magnesium hydroxide-aluminum hydroxide coprecipitate, magnesium aluminometasilicate, magnesium aluminosilicate, calcium silicate, non-crystalline silicon oxide hydrate, magnesium silicate, and magnesium silicate hydrate.
(5) The composite particles according to any one of (1) to (4), wherein the inorganic compound is calcium silicate.
(6) The composite particles according to any one of (1) to (5), wherein a pore size is 0.003 to 1 μm, and a pore volume is 1.9 to 3.9 cm$^3$/g.
(7) The composite particles according to any one of (1) to (6), wherein a retention rate of tocopherol acetate is 500 to 1000%.
(8) The composite particles according to any one of (1) to (7), wherein a weight average particle size is 30 to 250 μm.
(9) The composite particles according to any one of (1) to (8), further comprising starch.
(10) A molded article comprising the composite particles according to any one of (1) to (9) and an active ingredient.
(11) The molded article according to (10), wherein the active ingredient is an ingredient for a medicament or an ingredient for health food.
(12) A molded article comprising composite particles comprising a cellulose and an inorganic compound, and an active ingredient, wherein the active ingredient is a liquid having a viscosity at 25° C. of 3 to 10000 mPa·s, and the molded article contains 105 to 250 mg of the active ingredient per 500 mg of one molded article.
(13) The molded article according to (12), wherein the liquid ingredient is tocopherol acetate.

Advantageous Effects of Invention

The composite particles according to the present invention have a large apparent specific volume and pore volume, and a high retention rate of tocopherol acetate as an index of the liquid retention rate. Scattering properties are reduced by forming a composite product, providing good operability. Thereby, the composite particles of the present invention can be used as an adsorption carrier of the liquid ingredient. By forming a composite product, high fluidity after retention of the liquid can be provided, a uniformity in weight of the molded article and content of the active ingredient can be provided among molded articles, and a large content of the liquid ingredient can be contained in the molded article. In addition, the molded article according to the present invention has sufficient hardness, can prevent sticking and capping, and provide a molded article having low friability.

DESCRIPTION OF EMBODIMENTS

Figure 1:
FIG. 1 is an enlarged SEM photograph at a magnification of 500 times of Composite Particles B according to Example 2.

Hereinafter, an embodiment for implementing the present invention (hereinafter, simply referred to as "the present embodiment") is described in detail with reference to the drawings when necessary. The present embodiment below is only an example for describing the present invention, and is not intended to limit the present invention to the contents below. Moreover, the attached drawings show an example of the embodiment, and the present embodiment should not be construed to be limited to the drawings. The present invention can be properly modified without departing from the gist, and implemented.

The composite particles according to the present embodiment comprise a cellulose and an inorganic compound formed into a composite product and having a specific apparent specific volume.

In the present embodiment, the cellulose refers to fibrous materials containing a natural polymer obtained from natural products. In the present embodiment, the cellulose preferably has a crystal structure of a cellulose type I. Preferably, the cellulose has an average width of 2 to 30 μm and an average thickness of 0.5 to 5 μm. If the average width and average thickness of the cellulose are within the ranges above, preferably, the pore within the particle can be sufficiently developed by forming a composite product. More preferably, the cellulose has an average width of 2 to 25 μm and an average thickness of 1 to 5 μm.

The cellulose in the present invention includes microcrystalline cellulose. The microcrystalline cellulose used in the present invention is a white crystalline powder obtained by partially depolymerizing α-cellulose obtained as pulp obtained from a fibrous plant with mineral acid, and purifying the partially depolymerized product. The microcrystalline cellulose has various grades. In the present invention, the microcrystalline cellulose having a polymerization degree of 100 to 450 is preferable. As a commercially available product, "Ceolus" PH grade, "Ceolus" KG grade, and "Ceolus" UF grade (all made by Asahi Kasei Chemicals Corporation) can be used. The UF grade is most preferable.

Preferably, the cellulose has a volume average particle size of 10 to 100 μm. The volume average particle size is preferably 10 to 50 μm, and more preferably 10 to 40 μm.

The cellulose preferably has an average polymerization degree of 10 to 450. The average polymerization degree is more preferably 150 to 450.

In the present embodiment, the inorganic compound is not particularly limited as long as the inorganic compound is insoluble in water and has an apparent specific volume of 10 to 50 cm$^3$/g. For example, silicon dioxide hydrate, light anhydrous silicic acid, synthetic aluminum silicate, magnesium hydroxide-aluminum hydroxide co-precipitate, magnesium aluminometasilicate, magnesium aluminosilicate, calcium silicate, non-crystalline silicon oxide hydrate, magnesium silicate, and magnesium silicate hydrate are preferable. Preferably, the inorganic compound has a volume average particle size of 10 to 50 μm because the concentration of the dispersion liquid of the cellulose and the inorganic compound can be increased. Particularly preferably, the inorganic compound is calcium silicate. Calcium silicate is composed of CaO, SiO$_2$, and H$_2$O. Those represented by the formula $2CaO.3SiO_2.mSiO_2.nH_2O$ ($1<m<2$, $2<n<3$) are preferable. As a commercially available product, a product name Florite R (made by Tokuyama Corporation), a product name Florite RE (CaO$_2$ is 50% or more, CaO is 22% or more, available from Eisai Food & Chemical Co., Ltd.), and the like are available. Calcium silicate is a white powder, and water-insoluble. Calcium silicate is a substance having a high liquid absorbing ability and good compactibility. The volume average particle size is preferably 10 to 40 μm, and more preferably 20 to 30 μm.

From the viewpoint of prevention of sticking, it is thought that when the inorganic compound has a larger apparent specific volume and specific surface area, higher properties can be demonstrated. Light anhydrous silicic acid has higher physical properties described above than those of calcium silicate. As a result of extensive research of an inorganic compound used with the cellulose as the composite particles in the present invention, however, it was found that the highest sticking-preventing effect is demonstrated in the case where calcium silicate is used.

The present inventors found out that the inorganic compound and the cellulose are formed into a composite product to make the apparent specific volume as large as possible; thereby, a retention rate of tocopherol acetate as an index of the liquid retention rate can be maximized.

Single calcium silicate has a retention rate of tocopherol acetate of 800 to 900%, and has a high retention rate among the inorganic compounds. The retention rate of tocopherol acetate by the cellulose is 200 to 250%. For this reason, it is thought that a mixture having a retention rate of more than 800% cannot be obtained even if calcium silicate is simply mixed with the cellulose. It was found, however, that the pore within the particle is sufficiently developed by forming a composite product to provide a retention rate higher than a simple arithmetic average value.

As an example, the retention rate of tocopherol acetate is compared between a mixture of cellulose and calcium silicate, in which the amount of calcium silicate to be blended is approximately 50%, and the composite particles. In the case of the mixture, the logical value of the retention rate of tocopherol acetate is approximately 550%. Meanwhile, the composite particles having the same blending amount of calcium silicate has an extremely high retention rate of approximately 740%.

In other words, by forming the cellulose and calcium silicate into a composite product, the liquid retention rate is improved, and further, the properties of the cellulose are successfully given to the composite particles. Thereby, the composite particles having a high liquid retention rate and given compactibility and fluidity that the cellulose has can be provided.

Preferably, the composite particles according to the present embodiment contain 10 to 60 parts by mass of the cellulose and 40 to 90 parts by mass of the inorganic compound. More preferably, the composite particles according to the present embodiment contain 15 to 45 parts by mass of the cellulose and 55 to 85 parts by mass of the inorganic compound. If the inorganic compound is 40 parts by mass or more, a large intraparticle pore volume can be given to the obtained composite particles including the cellulose and the inorganic compound to provide sufficient liquid retention. Moreover, compression compactibility after retention of the liquid is improved. If the inorganic compound is 90 parts by mass or less, flushing properties can be suppressed, and variation in the weight of the molded article and the content of the active ingredient and reduction in compactibility can be suppressed.

Figure 9:
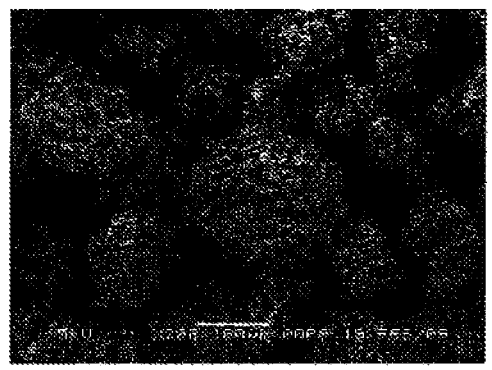
FIG. 9 is an enlarged SEM photograph at a magnification of 200 times of Composite Particles H according to Example 8.
Figure 10:
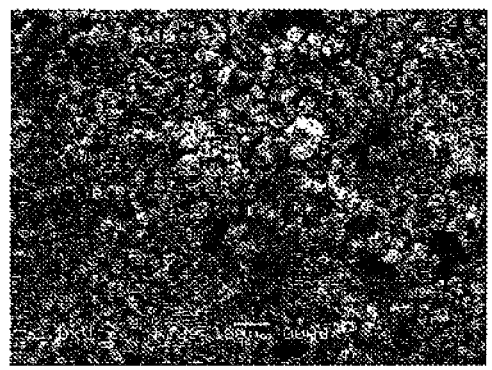
FIG. 10 is an enlarged SEM photograph at a magnification of 100 times of a mixture of cellulose and calcium silicate.

In the present embodiment, the composite particles are not simply a mixture of the cellulose and the inorganic compound. The composite particles need to contain a single aggregate larger than a single particle, the aggregate being composed of several particles of the cellulose and several particles of the inorganic compound. When the surfaces of the composite particles according to the present embodiment are observed using an SEM (magnification of 200 to 500 times), particles of the cellulose and particles of the inorganic compound are observed individually. It can be found that several particles of the cellulose and several particles of the inorganic compound collect to form the aggregate (see FIG. 9). For comparison, a simple mixture is shown in FIG. 10. The aggregate is larger than a single particle of the cellulose and a single particle of the inorganic compound. Meanwhile, in the simple mixture of the cellulose powder and the inorganic compound powder, primary particles of the cellulose and primary particles of the inorganic compound individually exist, and no aggregate is formed. For this reason, in the case of the simple mixture, high compactibility and fluidity as demonstrated by the composite particles according to the present embodiment are not obtained. Formation of the composite particles can be determined by observation with an SEM, or the weight proportion of the particles remaining on a sieve when the particles are sieved with the sieve having an opening of 75 μm. If the proportion of the particles remaining on the 75 μm sieve is 5 to 70% by weight, and preferably 10 to 70% by weight, it is determined that the composite particles are formed. The composite particles can have pores formed within the particle. Thereby, the composite particles can carry the amount of the liquid ingredient more than the amount of the liquid ingredient that can be carried by individual particles of the cellulose and individual particles of the inorganic compound. As formation of the composite product is progressed, the amount of the pores within the particles is increased, leading to a higher ability to carry the liquid ingredient. For example, the degree of formation of the composite product can be measured by comparing the retention rate of tocopherol acetate. In the simple physical mixture of the cellulose and the inorganic compound, the retention rate of tocopherol acetate is only an arithmetic average value based on the composition ratio of the cellulose and the inorganic compound. Meanwhile, as formation of the composite product is progressed, the amount of the pores within the particles is increased. For this reason, the composite particles have a higher retention rate of tocopherol acetate.

The composite particles according to the present embodiment need to have an apparent specific volume of 7 to 13 cm$^3$/g. At an apparent specific volume of 7 cm$^3$/g or more, the liquid retention rate is improved. At an apparent specific volume of 13 cm$^3$/g or less, increase in flushing properties can be suppressed, and variation in the content of the active ingredient and reduction in compactibility can be suppressed. More preferably, the apparent specific volume is 8 to 12 cm$^3$/g.

The composite particles according to the present embodiment preferably have a pore size of 0.003 to 1 µm. Here, the pore size means the size of the pore on the surface of the composite particle. More preferably, the pore size is 0.05 to 0.5 µm.

The composite particles according to the present embodiment preferably have a pore volume of 1.9 to 3.9 cm$^3$/g. Here, the pore volume means the volume of fine pores that the composite particles have. A pore volume of 1.9 cm$^3$/g or more improves the liquid retention rate. At a pore volume of 3.9 cm$^3$/g or less, increase in flushing properties can be suppressed, and variation in the content of the active ingredient and reduction in compactibility can be suppressed. More preferably, the pore volume is 2 to 3.5 cm$^3$/g.

The pore volume contributes to the compression compactibility of the composite particles and the liquid retention of the molded article. At a large pore volume, the composite particles are likely to be crushed during compression, leading to improved plastic deformability and enhanced hardness of the molded article. Moreover, a large pore volume promotes penetration of the liquid into the composite particles, leading to improved liquid retention.

Preferably, the composite particles according to the present embodiment have a porosity of 15 to 50%. Here, the porosity means a proportion of the pore volume to the volume of the composite particles. A porosity of 15% or more provides a high liquid retention rate, thus it is preferable. A porosity of 50% or less can suppress increase in flushing properties and reduction in compactibility, thus it is preferable. More preferably, the porosity is 20 to 40%.

The composite particles according to the present embodiment preferably have a weight average particle size of 30 to 250 µm. From the viewpoint of fluidity, the weight average particle size is preferably 30 µm or more. From the viewpoint of suppression in separation and segregation, the weight average particle size is preferably 250 µm or less. More preferably, the weight average particle size is 40 to 100 µm. Here, separation and segregation mean that the active ingredient is not uniformly mixed with the composite particles, and that a uniformly mixed state is not kept.

The composite particles according to the present embodiment preferably have a retention rate of tocopherol acetate of 500 to 1000%. At a high retention rate of tocopherol acetate, namely, a high liquid retention rate, the content of the active ingredient in the molded article can be increased. At a retention rate of tocopherol acetate less than 500%, the amount of the liquid to be carried is small. From the viewpoint of liquid retention, the retention rate of tocopherol acetate is preferably as high as possible, but approximately 1000% at best. The retention rate of tocopherol acetate is more preferably 600 to 1000%, and particularly preferably 700 to 1000%.

From the viewpoint of fluidity, the composite particles according to the present embodiment preferably have a repose angle of 45° or less. The repose angle is preferably as small as possible, and the lower limit is not particularly limited. From the viewpoint of suppression in separation and segregation of the active ingredient during continuous compression at a high speed, the repose angle is preferably 25°. More preferably, the repose angle is 25 to 40°. Similarly, from the viewpoint of fluidity, preferably, the composite particles after retention of the liquid have a repose angle of 45° or less, and preferably 25 to 40°.

The composite particles according to the present embodiment preferably have a hardness of 200 to 340 N. Here, the hardness is a value obtained by measurement of a cylindrical molded article obtained by compressing 0.5 g of the composite particles at a pressure of 10 MPa with a punch having a circular flat surface having a diameter of 1.1 cm by a Schleuniger hardness tester.

Preferably, the composite particles according to the present embodiment further include starch. Starch has binding properties, thus contributes to keeping a composite state of the cellulose and the inorganic compound. Thereby, a granulation state is fixed. Accordingly, addition of starch is preferable. As starch, for example, dextrin, soluble starch, corn starch, potato starch, partly pregelatinized starch, pregelatinized starch, and the like can be used. Those having binding properties are preferable. As starch contributing to improvement in disintegration properties, a "SWELSTAR (trademark) WB-1 (made by Asahi Kasei Chemicals Corporation)" is particularly preferable because the outer shell is a glue ingredient having binding properties and the inner shell is a disintegrable particle. 5 parts by mass to 15 parts by mass of starch is preferably contained based on 100 parts by mass of the composite particles including starch. At this time, 85 to 95 parts by mass of the microcrystalline cellulose and the inorganic compound in total are preferably contained.

The composite particles according to the present embodiment have a large apparent specific volume, a high liquid retention rate, and high fluidity. Further, the composite particles according to the present embodiment can be suitably used for a direct tableting method and a wet tableting method. The composite particles according to the present embodiment also have reduced scattering properties and high operability to prevent tableting problems such as sticking and capping.

The composite particles according to the present embodiment are particularly suitable for an active ingredient having low fluidity and difficulties to provide hardness of the tablet. Specific examples thereof include essence powders of over-the-counter drugs such as cold medicines and Kampo medicines, and drugs easy to be deactivated by a compression force or friction with an excipient such as enzymes and proteins.

The composite particles according to the present embodiment are also suitable for tablets easy to have tableting problems such as breakage or chips of the surface of the tablet, peel off from the inside, and cracks. Specific examples of the tablets include small tablets, non-circular deformed tablets having a portion such as a constriction of an edge to which a compression force is difficult to be uniformly applied, tablets containing a large amount of various drugs, and tablets containing coating granules.

Hereinafter, a method for producing the composite particles according to the present embodiment is described.

The composite particles according to the present embodiment are obtained by dispersing the cellulose and the inorganic compound in a medium, and drying the obtained dispersion liquid. Alternatively, the composite particles according to the present embodiment can also be obtained by strongly stirring the cellulose and the inorganic compound by a wet method (i.e., formation of a composite product, co-processing).

A raw material for the cellulose is natural products containing a cellulose. Examples of the raw material for the cellulose include wood materials, bamboo, wheat straw, rice straw, cotton, ramie, bagasse, kenaf, beet, hoya, and bacterial cellulose. The raw material may be of plant or animal origin, and two or more thereof may be mixed. Alternatively, the raw material may be hydrolyzed. Particularly in the case of hydrolysis, examples thereof include acid hydrolysis, alkali oxidative decomposition, hydrothermal decomposition, and steam explosion. These may be used in combination.

In the hydrolysis, a medium for dispersing the solid content containing the cellulose is not particularly limited as long as the medium is industrially used. As such medium, water or an organic solvent can be used. Examples of the organic solvent include alcohols such as methanol, ethanol, isopropyl alcohol, butyl alcohol, 2-methyl butyl alcohol, and benzyl alcohol; hydrocarbons such as pentane, hexane, heptane, and cyclohexane; and ketones such as acetone and ethyl methyl ketone. Particularly, the organic solvent is preferably those used for pharmaceuticals. Examples of the organic solvent include those classified as solvents in "Japanese Pharmaceutical Excipients Directory" (issued by Yakuji Nippo Limited). The medium is preferably water. Water and the organic solvents may be used in combination. Alternatively, the cellulose and the inorganic compound may be dispersed in one medium once, and the medium may be removed; then, the cellulose and the inorganic compound may be dispersed in a different medium.

The cellulose in the present invention preferably has an average width of 2 to 30 µm and an average thickness of 0.5 to 5 µm. The method is not particularly limited as long as it is a method for tearing the cellulose mainly in the longitudinal length. The average width and average thickness of the cellulose can be controlled within specific ranges by treating wood pulp with a high-pressure homogenizer, and when necessary, performing a mechanical treatment such as grinding and sorting, or combining these two properly. Alternatively, for example, a pulp whose cellulose has an average width of 2 to 30 µm and an average thickness of 0.5 to 5 µm may be selected and used. The volume average particle size of a water-dispersed cellulose is preferably 10 to 100 µm. The volume average particle size is preferably 10 to 50 µm, and more preferably 10 to 40 µm. Patent Literature 3 describes a cellulose for composing in which the cellulose dispersed in water has an L/D of 2.0 or more in a 10 to 100 µm fraction. As shown in Examples in Patent Literature 3, the cellulose cannot attain a high apparent specific volume as in the present application. Further, the cellulose of Patent Literature 3 is inferior to the composite product according to the present invention with respect to the pore volume and the retention rate of tocopherol acetate. The cellulose having a specific average width and average thickness is preferable for increasing the amount of the pores within the particles.

Examples of a method for obtaining a cellulose having a volume average particle size of 10 to 100 µm in the state of the cellulose dispersed in water include:

i) a method of shearing, grinding, crushing, and pulverizing a cellulose to adjust a particle size, ii) a method of performing a high pressure treatment such as explosion on a cellulose to separate the cellulose particles in the direction along their long axis, and when necessary, applying a shear force to adjust a particle size, and iii) a method of performing a chemical treatment on a cellulose to adjust a particle size.

Any of the methods described above may be used, and two or more methods described above may be used in combination. The methods i) and ii) may be performed by a wet method or a dry method. These wet and dry methods may be used in combination.

Examples of the methods i) and ii) include shearing methods using a stirring blade of a one-direction rotation type, a multi-axis rotation type, a reciprocal inversion type, a vertical movement type, a rotation+vertical movement type, or a piping type such as a portable mixer, a three-dimensional mixer, and a side-wall mixer; a jet type stirring/shearing method such as a line mixer; a treatment method using a high-shear homogenizer, a high-pressure homogenizer, and an ultrasonic homogenizer; and an axial rotation extrusion type shearing method such as a kneader.

Particularly, examples of a pulverizing method include a screen type pulverizing method such as a screen mill and a hammer mill, a blade rotation shearing screen type pulverizing method such as a flush mill, an air stream type pulverizing method such as a jet mill, a ball type pulverizing method such as a ball mill and a vibratory ball mill, and a blade stirring type pulverizing method. Two or more methods among them may be used in combination.

The volume average particle size of the cellulose can also be controlled within a desired range by adjusting a condition on a step of hydrolyzing or dispersing the cellulose, particularly, adjusting a stirring force applied to the solution containing the cellulose. Generally, if the concentrations of an acid and an alkali in the hydrolysis solution are increased or the reaction temperature is increased, the polymerization degree of the cellulose is likely to be reduced to provide a smaller volume average particle size of the cellulose in the dispersion liquid. If the stirring force applied to the solution is stronger, the cellulose particle is likely to have a smaller volume average particle size.

Next, a method for producing a dispersion liquid containing the cellulose and the inorganic compound is described. The dispersion liquid can be produced by dispersing the cellulose and the inorganic compound in a medium. Specifically, examples of the method include:

i) a method of adding a mixture of the cellulose and the inorganic compound in a medium to prepare a dispersion liquid, ii) a method of adding the inorganic compound to a cellulose dispersion liquid to prepare a dispersion liquid, iii) a method of adding the inorganic compound to a dispersion liquid prepared by mixing a third ingredient such as starch with cellulose particles to prepare a dispersion liquid, iv) a method of adding the inorganic compound to a mixture of a third ingredient such as starch and a cellulose dispersion liquid to prepare a dispersion liquid, and v) a method of adding the cellulose to a dispersion liquid having the inorganic compound added to prepare a dispersion liquid.

A method for adding the respective ingredients is not particularly limited as long as it is a method usually performed. Specifically, examples of the addition method include those using a small size suction transport apparatus, an air transport apparatus, a bucket conveyor, a pneumatic transport apparatus, a vacuum conveyer, a vibration type quantitative metering feeder, a spray, a funnel, or the like. The respective ingredients may be continuously added, or added in batch.

A mixing method is not particularly limited as long as it is a method usually performed. Specifically, a vessel rotation type mixer such as V-type, W-type, double cone type, and container tack type mixers, a stirring type mixer such as high speed stirring type, universal stirring type, ribbon type, pug type, and Nauta-type mixers, a high speed fluid type mixer, a drum type mixer, and a fluidized bed type mixer may be used. Alternatively, dispersing methods using vessel shaking type mixer such as a shaker, and a stirring blade of a one-direction rotation type, a multi-axis rotation type, a reciprocal inversion type, a vertical movement type, a rotation+vertical movement type, or a piping type such as a portable mixer, a three-dimensional mixer, a side-wall mixer, a jet type stirring/dispersing method such as a line mixer, a treatment method using a high-shear homogenizer, a high-pressure homogenizer, or an ultrasonic homogenizer, and an axial rotation extrusion type shearing method such as a kneader may be used, for example. Two or more methods among them may be used in combination.

The concentration of the cellulose, inorganic compound, and starch in the dispersion liquid obtained by the above-described operation is preferably 5 to 40% by mass. From the viewpoint of fluidity of the composite particles obtained by drying the dispersion liquid, the concentration is preferably 5% by mass or more. From the viewpoint of compression compactibility, the concentration is preferably 40% by mass or less. The concentration is more preferably 5 to 30% by mass, and still more preferably 5 to 20% by mass.

The dispersion liquid obtained by the above-described operation is dried to obtain the composite particles according to the present embodiment. A drying method is not particularly limited. Examples thereof include lyophilization, spray drying, drum drying, shelf drying, air stream drying, and vacuum drying. Two or more methods among them may be used in combination. A spraying method during spray drying may be any spray drying method such as a disc type drying method, a pressure nozzle type drying method, a compressed two-fluid nozzle type drying method, and a compressed four-fluid nozzle type drying method. Two or more methods among them may be used in combination.

During the spray drying, a slight amount of a water-soluble polymer and a surfactant may be added in order to reduce the surface tension of the dispersion liquid. In order to accelerate the vaporization rate of the medium, a foaming agent or a substance to generate a gas may be added, or a gas may be added to the dispersion liquid. Specific examples of the water-soluble polymer, the surfactant, the foaming agent, the substance to generate a gas, and the gas are shown below, respectively. The water-soluble polymer, the surfactant, and the substance to generate a gas may be added before drying, and the order of addition is not particularly limited. Two or more of water-soluble polymers, surfactants and the substances to generate a gas respectively may be used in combination.

Examples of the water-soluble polymer include water-soluble polymers described in "Japanese Pharmaceutical Excipients Directory" (issued by Yakuji Nippo Limited) such as hydroxypropyl cellulose, hydroxypropyl methylcellulose, polyacrylic acid, carboxyvinyl polymers, polyethylene glycol, polyvinyl alcohol, polyvinylpyrrolidone, methylcellulose, acacia, and starch paste.

Examples of the surfactant include those classified as a surfactant in "Japanese Pharmaceutical Excipients Directory" (issued by Yakuji Nippo Limited) such as phosphoruslipid, glycerin fatty acid ester, polyethylene glycol fatty acid ester, sorbitan fatty acid ester, polyoxyethylene hardened castor oil, polyoxyethylene cetyl ether, polyoxyethylene stearyl ether, polyoxyethylene nonylphenyl ether, polyoxyethylene polyoxypropylene glycol, polyoxyethylene sorbitan monolaurate, polysorbate, sorbitan monooleate, glyceride monostearate, monooxyethylene sorbitan monopalmitate, monooxyethylene sorbitan monostearate, polyoxyethylene sorbitan monooleate, sorbitan monopalmitate, and sodium lauryl sulfate.

Examples of the foaming agent include foaming agents described in "Japanese Pharmaceutical Excipients Directory" (issued by Yakuji Nippo Limited) such as tartaric acid, sodium hydrogencarbonate, potato starch, anhydrous citric acid, medical soap, sodium lauryl sulfate, lauric acid diethanolamide, and Lauromacrogol.

Examples of the substance to generate a gas include bicarbonates that generate a gas by pyrolysis such as sodium hydrogen carbonate and ammonium hydrogen carbonate; and carbonates that react with an acid to generate a gas such as sodium carbonate and ammonium carbonate. In use of the carbonates, the carbonates are preferably used with an acid. Examples of the acid include organic acids such as citric acid, acetic acid, ascorbic acid, and adipic acid; proton acids such as hydrochloric acid, sulfuric acid, phosphoric acid, and nitric acid; and Lewis acids such as boron fluoride. Particularly, those used in pharmaceuticals and foods are preferable.

As the gas, gases such as nitrogen, carbon dioxide, liquefied petroleum gas, and dimethyl ether may be impregnated into the dispersion liquid.

The composite particles according to the present embodiment are formed by simultaneously drying the cellulose and the inorganic compound in the state where the inorganic compound exists in the dispersion liquid containing the cellulose. It is thought that if the medium is vaporized in the state where the cellulose and the inorganic compound are uniformly associated, capillary condensation acts to aggregate the cellulose and the inorganic compound densely. Even if only the cellulose is dried and the inorganic compound is added to and mixed with the dried cellulose, or only the inorganic compound is dried and the cellulose is added to and mixed with the dried inorganic compound, a composite product is not formed, thus the aggregate structure cannot be obtained. In the case where the cellulose in the dispersion liquid has a specific average width and average thickness, the cellulose has a large suppressing effect on excessive aggregation of particles caused by capillary condensation during drying, and can provide a large pore volume within the composite particles. When the composite particles according to the present embodiment are produced, cellulose particles and inorganic compound particles also remain in the dried powders. These cellulose particles and inorganic compound particles may be used as they are without separation.

The molded article according to the present embodiment is obtained by molding the composite particles according to the present embodiment and an active ingredient. Hereinafter, the molded article according to the present embodiment is described.

In the molded article, the proportion of the active ingredient to be used is in the range of 0.001 to 99%, and the proportion of the composite particles to be used is in the range of 1 to 99.999%. From the viewpoint of ensuring an amount effective in treatment, the proportion of the active ingredient is preferably 0.001% or more. From the viewpoint of practical hardness, friability, and disintegration properties, the proportion of the active ingredient is preferably 99% or less. More preferably, the molded article contains 1 to 90% of the composite particles. In the case where the active ingredient is a liquid, tableting problems such as sticking and capping occur. For this reason, the content of the active ingredient in the molded article is limited. The composite product according to the present invention has high liquid retention and compactibility, and can be blended with more than 20% of a liquid ingredient. The proportion of the liquid ingredient is preferably 21 to 50%, and particularly preferably 21 to 30%. The largest content of tocopherol acetate in the commercially available molded articles at present is 100 mg/500 mg of the total amount of the tablet. No commercially available molded articles contain more than 20% of tocopherol acetate. By use of the composite product according to the present invention, at a blending amount of the liquid ingredient of 21 to 50%, the molded article can be downsized in the range of 250 to 480 mg. Moreover, at a weight of a tablet of 500 mg, the amount of the liquid ingredient can be increased in the range of 105 to 250 mg. The amount of the liquid ingredient is preferably 120 to 200 mg, and more preferably 120 to 150 mg.

The molded article according to the present embodiment can be processed by a known method such as granulation, sizing, and tableting. Particularly, the composite particles according to the present embodiment are suitable for molding by tableting. If the composite particles according to the present embodiment and the active ingredient are contained in the ranges as described above, a molded article having sufficient hardness can be produced by the direct tableting method. In addition to the direct tableting method, the composite particles according to the present embodiment are also suitable for a dry granule compression method, a wet granule compression method, a compression method with extragranular addition of an excipient, a method of producing a multicore tablet using a tablet which is compressed in advance as an inner core, and a method of layering a plurality of molded articles compressed in advance and compressing the layered molded articles again to produce a multilayer tablet.

In the present embodiment, examples of the active ingredient include ingredients for a medicament, ingredients for health food, pesticide ingredients, fertilizer ingredients, livestock food ingredients, food ingredients, cosmetic ingredients, dyes, flavoring agents, metals, ceramics, catalysts, and surfactants. Ingredients for a medicament and ingredients for health food are suitable active ingredients.

The ingredients for a medicament are used in substances orally administered such as antipyretic analgesic anti-inflammatory, sedative hypnotic, drowsiness preventing, dizziness suppressing, children's analgesic, stomachic, antacid, digestive, cardiotonic, antiarrhythmic, hypotensive, vasodilator, diuretic, antiulcer, intestinal function-controlling, bone-building, antitussive expectorant, antiasthmatic, antimicrobial, pollakiuria-improving, analeptic drugs, and vitamins. Active pharmaceutical ingredients may be used alone, or two or more of ingredients may be used in combination. Specifically, examples of the medicinal ingredients can include ingredients for a medicament described in "Japanese Pharmacopeia," "Japanese Pharmaceutical Codex (JPC)," "USP," "NF," and "EP" such as aspirin, aspirin aluminium, acetaminophen, ethenzamide, sasapyrine, salicylamide, lactylphenetidin, isotibenzyl hydrochloride, diphenylpyraline hydrochloride, diphenhydramine hydrochloride, difeterol hydrochloride, triprolidine hydrochloride, tripelenamine hydrochloride, thonzylamine hydrochloride, fenethazine hydrochloride, methdilazine hydrochloride, diphenhydramine salicylate, carbinoxamine diphenyldisulfonate, alimemazine tartrate, diphenhydramine tannate, diphenylpyraline teoclate, mebhydrolin napadisylate, promethazine methylenedisalicylate, carbinoxamine maleate, chlorpheniramine dl-maleate, chlorpheniramine d-maleate, difeterol phosphate, alloclamide hydrochloride, cloperastine hydrochloride, pentoxyverine citrate (carbetapentane citrate), tipepidine citrate, dibunate sodium, dextromethorphan hydrobromide, dextromethorphan-phenolphthalic acid, tipepidine hibenzate, chloperastine fendizoate, codeine phosphate, dihydrocodeine phosphate, noscapine hydrochloride, noscapine, dl-methylephedrine hydrochloride, dl-methylephedrine saccharin salt, potassium guaiacolsulfonate, guaifenesin, caffeine and sodium benzoate, caffeine, anhydrous caffeine, vitamin B1 and its derivatives and their salts, vitamin B2 and its derivatives and their salts, vitamin C and its derivatives and their salts, hesperidin and its derivatives and their salts, vitamin B6 and its derivatives and their salts, nicotinic acid amide, calcium pantothenate, aminoacetic acid, magnesium silicate, synthetic aluminum silicate, synthetic hydrotalcite, magnesia oxide, dihydroxyaluminum-aminoacetate (aluminum glycinate), aluminium hydroxide gel (as dried aluminium hydroxide gel), dried aluminium hydroxide gel, aluminium hydroxide-magnesium carbonate mixed dried gel, aluminium hydroxide-sodium hydrogen carbonate coprecipitation products, aluminium hydroxide-calcium carbonate-magnesium carbonate coprecipitation products, magnesium hydroxide-potassium aluminum sulfate coprecipitation products, magnesium carbonate, magnesium aluminometasilicate, ranitidine hydrochloride, cimetidine, famotidine, naproxen, diclofenac sodium, piroxicam, azulene, indometacin, ketoprofen, ibuprofen, difenidol hydrochloride, diphenylpyraline hydrochloride, diphenhydramine hydrochloride, promethazine hydrochloride, meclizine hydrochloride, dimenhydrinate, diphenhydramine tannate, fenethazine tannate, diphenylpyraline teoclate, diphenhydramine fumarate, prometthazine methylenedisalicylate, scopolamine hydrobromide, oxyphencyclimine hydrochloride, dicyclomine hydrochloride, methixene hydrochloride, atropine methylbromide, anisotropine methylbromide, spocolamine methylbromide, methyl-1-hyoscyamine bromide, methylbenactyzium bromide, belladonna extract, isopropamide iodide, diphenylpiperidinomethyldioxolan iodide, papaverine hydrochloride, aminobenzoic acid, cesium oxalate, ethyl piperidinoacetylaminobenzoate, aminophyllin, diprophylline, theophylline, sodium hydrogen carbonate, fursultiamine, isosorbide nitrate, ephedrine, cefalexin, ampicillin, sulfixazole, sucralfate, allyl isopropylacetyl urea, bromovalerylurea and the like, ephedra herb, Nandina fruit, yellow bark, polygala root, licorice, platycodon root, plantago seed, plantago herb, senega root, fritillaria bulb, fennel, phellodendron bark, coptis rhizome, zedoary, matricaria, cassia bark, gentian, oriental bezoar, beast gall (containing bear bile), adenophorae radix, ginger, atractylodes lancea rhizome, clove, citrus unshiu peel, atractylodes rhizome, earthworm, panax rhizome, ginseng, japanese valerian, moutan bark, zanthoxylum fruit and extracts thereof, insulin, vasopressin, interferon, urokinase, serratio peptidase, and somatostatin. One selected from the above may be used alone, or two or more ingredients selected from the above may be used in combination.

The ingredients for health food are not limited as long as these are an ingredient blended for the purpose of augmenting. Examples thereof include powdered green juice, aglycone, agaricus, ashwagandha, astaxanthin, acerola, amino acids (valine, leucine, isoleucine, lysine, methionine, phenylalanine, threonine, tryptophan, histidine, cystine, tyrosine, arginine, alanine, aspartic acid, powdered seaweed, glutamine, glutamic acid, glycin, proline, serine, etc.), alginic acid, *ginkgo biloba* extract, sardine peptides, turmeric, uronic acid, echinacea, Siberian ginseng, oligosaccharides, oleic acid, nucleoproteins, dried skipjack peptides, catechin, potassium, calcium, carotenoid, garcinia cambogia, L-carnitine, chitosan, conjugated linoleic acid, Aloe arborescens, Gymnema sylvestre extract, citric acid, Orthosiphon stamineus, glycerides, glycenol, glucagon, curcumin, glucosamine, L-glutamine, chlorella, cranberry extract, Uncaria tomentosa, germanium, enzymes, Korean ginseng extract, coenzyme Q10, collagen, collagen peptides, coleus blumei, chondroitin, powdered psyllium husks, Crataegi fructus extract, saponin, lipids, L-cystine, Japanese basil extract, citrimax, fatty acids, phytosterol, seed extract, spirulina, squalene, Salix alba, ceramide, selenium, St. John's wort extract, soy isoflavone, soy saponin, soy peptides, soy lecithin, monosaccharides, proteins, chaste tree extract, iron, copper, docosahexaenoic acid, tocotrienol, nattokinase, Bacillus natto culture extract, sodium niacin, nicotine acid, disaccharides, lactic acid bacterium, garlic, saw palmetto, sprouted rice, pearl barley extract, herb extract, valerian extract, pantothenic acid, hyaluronic acid, biotin, chromium picolinate, vitamin A and A2, vitamin B1, B2 and B6, vitamin B12, vitamin C, vitamin D, vitamin E, vitamin K, hydroxytyrosol, bifidobacterium, beer yeast, fructo oligosaccharides, flavonoid, Butcher's broom extract, black cohosh, blueberry, prune concentrate, proanthocyanidin, proteins, propolis, bromelain, probiotics, phosphatidylcholine, phosphatidylserine, β-carotene, peptides, safflower extract, Grifola frondosa extract, maca extract, magnesium, milk thistle, manganese, mitochondria, mineral, mucopolysaccharides, melatonin, Fomes yucatensis, powdered melilot extract, molybdenum, vegetable powder, folic acid, lactose, lycopene, linolic acid, lipoic acid, phosphorus, lutein, lecithin, rosmarinic acid, royal jelly, DHA, and EPA The active ingredient may be any form of powdery, crystalline, liquid, and semi-solid forms. A liquid active ingredient is suitable. The active ingredient may be coated or encapsulated for control of elution, reduction in bitterness, or the like. In use of the active ingredient, the active ingredient may be dissolved, suspended, or emulsified in a medium. A plurality of active ingredients may be used in combination.

Examples of the liquid active ingredient include ingredients for a medicament described in "Japanese Pharmacopeia," "JPC," "USP," "NF," and "EP" such as teprenone, indomethacin-farnesyl, menatetrenone, phytonadione, vitamin A oil, fenipentol, vitamins such as vitamin D and vitamin E, higher unsaturated fatty acids such as DHA (docosahexaenoic acid), EPA (eicosapentaenoic acid), and liver oil, coenzyme Qs, and oil-soluble flavorings such as orange, lemon, and peppermint oils. Moreover, vitamin E has various homologues and derivatives thereof. Examples thereof can include dl-α-tocopherol, dl-α-tocopherol acetate, tocopherol acetate, and d-α-tocopherol acetate. The homologues and derivatives of vitamin E are not particularly limited as long as these are a liquid at 25° C. These having a viscosity in the range of 3 to 10000 mPa·s are preferable. If a homologue or derivative of vitamin E has a proper viscosity, it preferably provides a good balance between compactibility and fluidity of the composite particles after the liquid ingredient is carried by the composite product. Tocopherol acetate is particularly preferable.

Examples of the semi-solid active ingredient can include, Kampo medicines or crude drug extracts such as earthworm, licorice, cassia bark, peony root, moutan bark, japanese valerian, zanthoxylum fruit, ginger, citrus unshiu peel, ephedra herb, nandina fruit, yellow bark, polygala root, platycodon root, plantago seed, plantago herb, shorttube lycoris, senega root, fritillaria bulb, fennel, phellodendron bark, coptis rhizome, zedoary, matricaria, gentian, oriental bezoar, beast gall, adenophorae radix, ginger, atractylodes lancea rhizome, clove, citrus unshiu peel, atractylodes rhizome, panax rhizome, ginseng, kakkonto, keishito, kousosan, saiko-keishito, shosaikoto, shoseiryuto, bakumondoto, hangekobokuto, and maoto, an oyster meat essence, propolis or an extract thereof, and coenzyme Qs.

The crystal of the active ingredient after molding may have the same shape as that before molding, or may have a shape different from that before molding. Preferably, the shape of the crystal after molding is the same as that before molding from the viewpoint of stability.

In addition to the active ingredient and the composite particles, the molded article according to the present embodiment freely contains excipients such as an excipient, a disintegrant, a binder, a fluidizing agent, a lubricant, a corrigent, a flavoring agent, a coloring agent, and a sweetener when necessary. Two or more excipients among them may be used in combination.

Examples of the excipient include those classified as an excipient in "Japanese Pharmaceutical Excipients Directory" (issued by Yakuji Nippo Limited) such as acrylated starch, L-asparagic acid, aminoethyl sulfonic acid, aminoacetate, wheat gluten (powder), acacia, powdered acacia, alginic acid, sodium alginate, pregelatinized starch, inositol, ethyl cellulose, ethylene-vinyl acetate copolymer, sodium chloride, olive oil, kaolin, cacao butter, casein, fructose, light gravel granule, carmellose, carmellose sodium, silicon dioxide hydrate, dry yeast, dried aluminum hydroxide gel, dried sodium sulfate, dried magnesium sulfate, agar, agar powder, xylitol, citric acid, sodium citrate, disodium citrate, glycerin, calcium glycerophosphate, sodium gluconate, L-glutamine, clay, clay grain, croscarmellose sodium, crospovidone, magnesium aluminosilicate, calcium silicate, magnesium silicate, light anhydrous silicic acid, light liquid paraffin, cinnamon powder, microcrystalline cellulose, microcrystalline cellulose-carmellose sodium, microcrystalline cellulose (grain), brown rice malt, synthetic aluminum silicate, synthetic hydrotalcite, sesame oil, wheat flour, wheat starch, wheat germ powder, rice powder, rice starch, potassium acetate, calcium acetate, cellulose acetate phthalate, safflower oil, white beeswax, zinc oxide, titanium oxide, magnesium oxide, β-cyclodextrin, dihydroxyaluminum amino acetate, 2,6-dibutyl-4-methylphenol, dimethylpolysiloxane, tartaric acid, potassium hydrogen tartrate, plaster, sucrose fatty acid ester, magnesium hydroxide-aluminum hydroxide co-precipitate, aluminum hydroxide gel, aluminum hydroxide/sodium hydrogen carbonate coprecipitate, magnesium hydroxide, squalane, stearyl alcohol, stearic acid, calcium stearate, polyoxyl stearate, magnesium stearate, purified gelatine, purified shellac, purified sucrose, purified sucrose spherical granulated powder, cetostearyl alcohol, polyethylene glycol 1000 monocetyl ether, gelatine, sorbitan fatty acid ester, D-sorbitol, tricalcium phosphate, soybean oil, unsaponified soy bean, soy bean lecithin, powdered skim milk, talc, ammonium carbonate, calcium carbonate, magnesium carbonate, neutral anhydrous sodium sulfate, low substitution degree hydroxypropylcellulose, dextran, dextrin, natural aluminum silicate, corn starch, powdered tragacanth, silicon dioxide, NEWKAL-GEN 204, calcium lactate, lactose, par filler 101, white shellac, white vaseline, white clay, sucrose, sucrose/starch spherical granulated powder, naked barley green leaf extract powder, dried powder of bud and leaf juice of naked barley, honey, paraffin, potato starch, semi-digested starch, human serum albumin, hydroxypropyl starch, hydroxypropylcellulose, hydroxypropylcellulose, hydroxypropyl methylcellulose phthalate, phytic acid, glucose, glucose hydrate, partially pregelatinized starch, pullulan, propylene glycol, starch syrup of reduced malt sugar powder, powdered cellulose, pectin, bentonite, sodium polyacrylate, polyoxyethylene alkyl ethers, polyoxyethylene hydrogenated castor oil, polyoxyethylene (105) polyoxypropylene (5) glycol, polyoxyethylene (160) polyoxypropylene (30) glycol, sodium polystyrene sulfonate, polysorbate, polyvinylacetal diethylamino acetate, polyvinylpyrrolidone, polyethylene glycol (molecular weight of 1500 to 6000), maltitol, maltose, D-mannitol, water candy, isopropyl myristate, anhydrous lactose, anhydrous dibasic calcium phosphate, anhydrous dibasic calcium phosphate granulated substance, magnesium aluminometasilicate, methyl cellulose, cottonseed powder, cotton oil, haze wax, aluminum monostearate, glyceryl monostearate, sorbitan monostearate, pharmaceutical carbon, peanut oil, aluminum sulfate, calcium sulfate, granular corn starch, liquid paraffin, dl-malic acid, calcium monohydrogen phosphate, calcium hydrogenphosphate, calcium hydrogenphosphate granulated substance, sodium hydrogenphosphate, potassium dihydrogen phosphate, calcium dihydrogen phosphate, and sodium dihydrogen phosphate.

Examples of the disintegrant include those classified as a disintegrant in "Japanese Pharmaceutical Excipients Directory" (issued by Yakuji Nippo Limited) such as croscarmellose sodium, carmellose, carmellose calcium, carmellose sodium, celluloses such as low substitution degree hydroxypropylcellulose, starches such as sodium carboxymethyl starch, hydroxypropyl starch, rice starch, wheat starch, corn starch, potato starch, and partly pregelatinized starch, and synthetic polymers such as crospovidone and crospovidone copolymer.

Examples of the binder include those classified as a binder in "Japanese Pharmaceutical Excipients Directory" (issued by Yakuji Nippo Limited) sugars such as sucrose, glucose, lactose and fructose, sugar alcohols such as mannitol, xylitol, maltitol, erythritol, and sorbitol, water-soluble polysaccharides such as gelatine, pullulan, carrageenan, locust bean gum, agar, glucomannan, xanthan gum, tamarind gum, pectin, sodium alginate, and acacia, celluloses such as microcrystalline cellulose, powdered cellulose, hydroxypropylcellulose and methyl cellulose, starches such as cornstarch, potato starch, pregelatinized starch and starch paste, synthetic polymers such as polyvinylpyrrolidone, carboxyvinyl polymer and polyvinyl alcohol, and inorganic compounds such as calcium hydrogenphosphate, calcium carbonate, synthetic hydrotalcite, and magnesium alumino silicate.

Examples of the fluidizing agent include those classified as a fluidizing agent in "Japanese Pharmaceutical Excipients Directory" (issued by Yakuji Nippo Limited) such as silicon compounds such as silicon dioxide hydrate and light anhydrous silicic acid, wet silicas such as sodium silicates, calcium silicate, and sodium stearyl fumarate (trade name "PRUV" made by JRS).

Examples of the lubricant include those classified as a lubricant in "Japanese Pharmaceutical Excipients Directory" (issued by Yakuji Nippo Limited) such as magnesium stearate, calcium stearate, stearic acid, sucrose fatty acid ester, talc, Fujicalin, and sodium stearyl fumarate (trade name "PRUV" made by JRS).

Examples of the corrigent include those classified as a corrigent in "Japanese Pharmaceutical Excipients Directory" (issued by Yakuji Nippo Limited) such as glutamic acid, fumaric acid, succinic acid, citric acid, sodium citrate, tartaric acid, malic acid, ascorbic acid, sodium chloride, and 1-menthol.

Examples of the flavoring agent include those classified as aromatics and flavoring agents in "Japanese Pharmaceutical Excipients Directory" (issued by Yakuji Nippo Limited) such as orange, vanilla, strawberry, yogurt, menthol, oils such as fennel oil, cinnamon bark oil, orange peel oil, and peppermint oil, and green tea powder.

Examples of the colorant include those classified as a colorant in "Japanese Pharmaceutical Excipients Directory" (issued by Yakuji Nippo Limited) such as edible dyes such as edible red 3, edible yellow 5, and edible blue 1, sodium copper chlorophyllin, titanium oxide, and riboflavin.

Examples of the sweetener include those classified as a sweetener in "Japanese Pharmaceutical Excipients Directory" (issued by Yakuji Nippo Limited) such as aspartame, saccharin, dipotassium glycyrrhizinate, stevia, maltose, maltitol, starch syrup, and powdered sweet hydrangea leaf.

Examples of a form of the molded article include solid preparations such as tablets, powders, subtle granules, granules, and pills when the molded article is used for pharmaceuticals.

Hereinafter, a tablet is described as a suitable specific example of the molded article according to the present embodiment.

The tablet refers to a molded article containing the composite particles according to the present embodiment, the active ingredient, and when necessary other excipients, and obtained by tableting. The composite particles according to the present embodiment have high compression compactibility. Accordingly, a tablet for practical use can be obtained at a relatively low compression force. The composite particles according to the present embodiment can be molded and tableted at a low compression force. For this reason, the tablet can keep gaps (water introducing pipes) inside thereof. Such a tablet is suitable for an orally disintegrating tablet rapidly disintegrated in an oral cavity. In addition, the composite particles according to the present embodiment are suitable for multilayer tablets and core tablets obtained by compressing ingredients in several compositions at one stage or at multi stages. The composite particles according to the present embodiment have high effects of imparting high hardness to the molded article, and suppressing tableting problems, peel off between interlayers, and cracks. Further, the composite particles according to the present embodiment themselves have high dividing properties, thus a tablet formed of the composite particles according to the present embodiment is easy to be divided uniformly. Accordingly, the composite particles according to the present embodiment are also suitable for a scored tablet and the like.

The composite particles according to the present embodiment have a porous structure, and the composite particles themselves have high retention of the liquid ingredient such as fine particle drugs, suspended drugs, and liquid ingredients. For this reason, the molded article of the composite particles according to the present embodiment also has high retention of the liquid ingredient. For this reason, when a suspended or liquid ingredient is layered and coated on the tablet, the tablet also has a preventive effect on peel off of an outer layer such as a coating layer. Accordingly, the composite particles according to the present embodiment are also suitable for a layered tablet and a tablet having a coating layer (such as sugar-coated tablets, and tablets having a layered ingredient such as calcium carbonate).

Hereinafter, a method of producing a molded article containing the active ingredient and the composite particles according to the present embodiment is described. This is only an example, and the present invention is not limited to the description below.

Examples of a method for molding a molded article include a method of mixing the active ingredient with the composite particles according to the present embodiment, and compressing the mixture. At this time, the excipients other than the above-described active ingredient may be blended when necessary. The order of addition is not particularly limited. Examples of the method include:

1) a method in which the active ingredient is mixed with the composite particles according to the present embodiment and, when necessary, an excipient in batch, and the mixture is compressed;
2) a method in which the active ingredient is mixed with an excipient such as a fluidizing agent or a lubricant, and then mixed with the composite particles according to the present invention and, when necessary, an additional excipient, and the mixture is compressed; and
3) a method in which a lubricant is further mixed with the mixed powder for compression obtained by 1) or 2), and the obtained mixture is compressed.

A method for adding ingredients is not particularly limited as long as the method is a method usually performed. The ingredients may be added continuously or in batch using a small size suction transport apparatus, an air transport apparatus, a bucket conveyor, a pneumatic transport apparatus, a vacuum conveyer, a vibration type quantitative metering feeder, a spray, a funnel, or the like.

A mixing method is not particularly limited as long as the method is a method usually performed. A vessel rotation type mixer such as V-type, W-type, double cone type, and container tack type mixers, or a stirring type mixer such as high speed stirring type, universal stirring type, ribbon type, pug type, and Nauta-type mixers, a high speed fluid type mixer, a drum type mixer, or a fluidized bed type mixer may be used. Alternatively, a vessel shaking type mixer such as a shaker can be used.

A compression method is not particularly limited as long as the method is a method usually performed. The method may be a method of compressing ingredients into a desired shape using a die and a punch, or a method of compressing ingredients into a sheet form in advance and cutting the sheet into a desired shape. A usable compression machine is, for example, a compressor such as a hydrostatic press, a roller type press such as a briquetting roller type press or a smoothing roller type press, a single-punch tableting machine, or a rotary tableting machine.

In the case where an active ingredient poorly-soluble in water is used, generally, examples of the compression method include:
A) a method in which the active ingredient is pulverized, and mixed with the composite particles according to the present embodiment and, when necessary, other ingredient; and the obtained mixture is compressed; and
B) a method in which the active ingredient is dissolved or dispersed in water, an organic solvent, or a solubilizing agent, and mixed with the composite particles according to the present embodiment and, when necessary, other excipients; when necessary, water or the organic solvent is removed; and the obtained mixture is compressed.

The composite particles according to the present embodiment are suitable for the above-described method B). In the method B), the active ingredient poorly-soluble or insoluble in water is once dissolved or dispersed. For this reason, the active ingredient can be carried by the composite particles securely. Thereby, separation or elution of the active ingredient during compression can be prevented to suppress sticking. The composite particles according to the present embodiment have high compression compactibility and fluidity. For this reason, in the case of the method B), the composite particles according to the present embodiment can be formed into a tablet at little variation in the weight by the compression.

The method B) is more suitable in the case where the active ingredient in the drug is used for pharmaceuticals and a liquid medium such as polyethylene glycol is used in combination as a dispersion medium. Polyethylene glycol or the like is used in order to keep the efficacy of the active ingredient which is easily metabolizable in the liver by coating the active ingredient with polyethylene glycol in the blood when the active ingredient is absorbed in a human body.

In the method B), in order to assist dissolution, it is effective to use a water-soluble polymer or a surfactant as a solubilizing agent in combination to disperse the active ingredient in a medium.

The organic solvent is not particularly limited as long as it is used for pharmaceuticals. Examples of the organic solvent include those classified as a solvent in "Japanese Pharmaceutical Excipients Directory" (issued by Yakuji Nippo Limited) such as alcohols such as methanol and ethanol, and ketones such as acetone. Two or more organic solvents among them are freely used in combination.

Examples of the water-soluble polymer as the solubilizing agent in the method B) include water-soluble polymers described in "Japanese Pharmaceutical Excipients Directory" (issued by Yakuji Nippo Limited) such as hydroxypropyl cellulose, hydroxypropyl methylcellulose, polyacrylic acid, carboxyvinyl polymer, polyethylene glycol, polyvinyl alcohol, polyvinylpyrrolidone, methylcellulose, ethylcellulose, acacia, and starch paste. Two or more water-soluble polymers among them are freely used in combination.

Examples of oils and fats as the solubilizing agent include oils and fats described in "Japanese Pharmaceutical Excipients Directory" (issued by Yakuji Nippo Limited) such as monoglyceride stearate, triglyceride stearate, sucrose stearic acid ester, paraffins such as liquid paraffin, carnauba wax, hydrogenated oils such as hydrogenated castor oil, castor oil, stearic acid, stearyl alcohol, and polyethylene glycol. Two or more oils and fats among them are freely used in combination.

Examples of the surfactant in the solubilizing agent include those classified as a surfactant in "Japanese Pharmaceutical Excipients Directory" (issued by Yakuji Nippo Limited) such as phospholipid, glycerin fatty acid ester, polyethylene glycol fatty acid ester, sorbitan fatty acid ester, polyoxyethylene hardened castor oil, polyoxyethylene cetyl ether, polyoxyethylene stearyl ether, polyoxyethylene nonylphenyl ether, polyoxyethylene polyoxypropylene glycol, polyoxyethylene sorbitansan monolaurate, polysorbate, sorbitan monooleate, glyceride monostearate, monooxyethylene sorbitansan monopalmitate, monooxyethylene sorbitan monostearate, polyoxyethylene sorbitan monooleate, sorbitan monopalmitate, and sodium lauryl sulfate. Two or more surfactants among them are freely used in combination.

In the method B), a dissolving or dispersing method is not particularly limited as long as it is a dissolving or dispersing method usually performed. A stirring/mixing method using a stirring blade of a one-direction rotation type, a multi-axis rotation type, a reciprocal inversion type, a vertical movement type, a rotation+vertical movement type, or a piping type such as a portable mixer, a three-dimensional mixer, and a side-wall mixer; a jet type stirring/mixing method such as a line mixer; a gas-blowing stirring/mixing method; a mixing method using a high-shear homogenizer, a high-pressure homogenizer, or an ultrasonic homogenizer; or a vessel shaking type mixing method using a shaker, or the like may be used.

The composite particles according to the present embodiment have a porous structure, and the composite particles themselves have high retention of the drug. For this reason, the particles carrying the drug within pores may be used as they are as fine granules, may be granulated as used for granules, or may be compressed.

A method for carrying a drug is not particularly limited as long as it is a known method. Examples of the method include:

i) a method in which the composite particles according to the present embodiment are mixed with a fine particle drug to be carried within pores;

ii) a method in which the composite particles according to the present embodiment are mixed with a powdery drug at a high speed to be forcibly carried within pores;

iii) a method in which the composite particles according to the present embodiment are once mixed with a drug prepared as a solution or a dispersion liquid, the drug is carried within pores, and the obtained one is dried if necessary;

iv) a method in which the composite particles according to the present embodiment are mixed with a sublimation drug, and the mixture is heated and/or the pressure is reduced, thereby, the drug is sublimated and adsorbed within pores; and v) a method in which the composite particles according to the present embodiment are mixed with a drug before or during heating, and molten.

Two or more methods as described above may be used in combination.

Besides use as the tablet thus compressed, the composite particles according to the present embodiment may be used as granules or powders particularly in order to improve fluidity, blocking resistance, and aggregation resistance because the composite particles according to the present embodiment also have high retention of a solid or liquid ingredient. The above-described fine granules and the granules may be further coated.

As a method for producing granules and powders, the same effect is obtained even if any of dry granulation, wet granulation, heating granulation, spray drying, and micro-encapsulation is used, for example.

Moreover, the composite particles according to the present embodiment have proper moisture retention and oil retention. Accordingly, other than the excipient, the composite particles according to the present embodiment can be used as a core particle for layering and coating, and have a suppressing effect on aggregation of particles in a layering or coating step. The layering and coating may be a dry method or a wet method.

The composite particles according to the present embodiment are also used for foods such as confectionery, health foods, texture-improving agents, and dietary fiber-reinforcing agent, cake makeups, bath agents, animal drugs, diagnostic reagents, agricultural chemicals, fertilizers, and ceramic catalysts, and the like.

EXAMPLES

The present invention is described based on Examples. Embodiments of the present invention are not limited to the description of these Examples. In Examples and Comparative Examples, methods for measuring physical properties are as follows.

(1) Average Width of Cellulose ($\mu m$)

Cellulose primary particles formed of a natural cellulose were dried when necessary, and placed on a sample stage to which a carbon tape was attached. Platinum palladium was vacuum deposited (the membrane thickness of the deposited membrane at this time was 20 nm or less). Using a JSM-5510LV (trade name) made by JASCO Corporation, the cellulose primary particles were observed at an accelerating voltage of 6 kV and at a magnification of 250 times. A short diameter in the vicinity of the center of a long diameter of a cellulose particle was considered as a representative width, and the width was measured. The widths of three representative cellulose primary particles were measured, and the average was defined as the average width of the cellulose.

(2) Average Thickness of Cellulose ($\mu m$)

Cellulose primary particles formed of a natural cellulose were dried when necessary, and placed on a sample stage to which a carbon tape was attached. Gold was vacuum deposited. Then, using a focused ion beam processing apparatus (made by Hitachi, Ltd., FB-2100 (trade name)), a cross section of the cellulose primary particles was cut out with a Ga ion beam, and observed at an accelerating voltage of 6 kV and a magnification of 1500 times. A shorter diameter in the cross section of the cellulose particles was measured, and the obtained value was defined as the thickness (the cross section was cut out such that a longer diameter corresponded to the short diameter of the cellulose particle). The thicknesses of three representative cellulose primary particles were measured, and the average value thereof was defined as the thickness of the cellulose.

(3) Volume Average Particle Size of Cellulose or Inorganic Compound ($\mu m$)

The cellulose or the inorganic compound was dispersed in water to prepare a dispersion liquid. The volume average particle size of the cellulose or inorganic compound was defined as a 50% cumulative volume of particles in the dispersion liquid measured using a laser diffraction particle size distribution analyzer (made by HORIBA, Ltd., LA-910 (trade name)) wherein a measurement mode at 4 stirrings and 5 circulations was selected and the measurement condition was the transmittance of around 85%, an ultrasonic treatment for 1 minute, and the refractive index of 1.20. The measurement value as obtained above does not always correlate with the particle size distribution of dried particles obtained by the following Ro-Tap type apparatus because the measurement principles are totally different from each other. The volume average particle size measured by laser diffraction is measured from volume frequencies depending on the long diameter of fibrous particles while the weight average particle size obtained by the Ro-Tap type apparatus depends on the short diameter of fibrous particles because the obtained powder is shaken on a sieve and fractionated. Thus, there is a case that the value measured by the laser diffraction type apparatus depending on the long diameter of fibrous particles is larger than that measured by the Ro-Tap type apparatus depending on the short diameter of fibrous particles.

(4) Weight Average Particle Size of Composite Particles ($\mu m$)

10 g of a powder sample (dried composite particles) was sieved for 10 minutes using a Ro-Tap type sieve shaker (made by Taira Kosakusho Ltd., trade name "Sieve Shaker type A") with a JIS standard sieve (Z8801-1987) to measure particle size distribution, and the weight average particle size of the powder sample was defined as a 50% cumulative weight particle size. The particle size distribution was determined using a 300 μm sieve, a 212 μm sieve, a 177 μm sieve, a 150 μm sieve, a 106 μm sieve, a 75 μm sieve, and a 38 μm sieve.

(5) Pore Size (μm), Intraparticle Pore Volume ($Cm^3/g$), Porosity (%)

Pore distribution was determined using a trade name "Autopore type 9520" made by SHIMADZU Corporation according to mercury porosimetry. Approximately 0.03 g to 0.05 g of each of sample powders used in the measurement was placed in a standard cell, and the pore distribution was measured twice on the condition of an initial pressure of 7 kPa (corresponding to approximately 1 psia, pore diameter of approximately 18 μm). From the obtained pore distribution, a volume at a pore size in the specific range of 0.003 to 1.0 μm was calculated as the pore volume. The porosity is the proportion of the pore volume to the volume of the sample when mercury is pressed into pores having a diameter of approximately 180 μm at an initial atmospheric pressure.

(6) Repose Angle (°)

Using a Sugihara-type repose angle measuring instrument (slit size depth 10×width 50×height 140 mm, a protractor was set at a position of 50 mm in width), a sample was continuously deposited in a measurement part little by little (3 g/min as a guideline) with an electromagnetic feeder (MF-1 t e/TSUTSUI SCIENTIFIC INSTRUMENTS CO., LTD.). Thus, an inclined surface was formed. Immediately when an excessive sample started falling and the inclined surface became substantially linear, the feeder was turned off. The angle of the inclined surface was measured with the set protractor, and defined as the repose angle.

(7) Method for Compressing Sample 0.5 g of a sample was weighed, and placed in a die (Kikusui Seisakusho Ltd., a material used was SUS2,3). The sample was compressed with a punch having a circular flat surface having a diameter of 1.1 cm (made by Kikusui Seisakusho Ltd., a material of SUS2,3 was used) until the pressure reached 10 MPa (made by AIKOH ENGINEERING CO., LTD., a trade name "PCM-1A", compression rate of 1 cm/min), and kept at a target pressure for 10 seconds to produce a cylindrical molded article.

(8) Hardness of Tablet (N)

Using a Schleuniger hardness tester (made by Freund Corporation, trade name "8M type"), a load was applied to a cylindrical molded article or a tablet in the diameter direction of the cylindrical molded article or tablet, and the load when the cylindrical molded article or tablet was broken was measured. The hardness of the tablet was defined as the average value obtained from ten samples.

(9) Apparent Specific Volume ($Cm^3/g$)

A 25 $cm^3$ container was set in a Scott Volumeter (made by VWR SCIENTIFIC, S64985 type). Next, using an electromagnetic feeder (MF-1 t e/TSUTSUI SCIENTIFIC INSTRUMENTS CO., LTD.), a sample was put into the container at a rate of 10 to 20 g/min. When the sample overflowed from the set container, the container was taken out. An excessive amount of the sample was leveled off, and the mass of the sample was measured. The apparent specific volume was defined as a value ($cm^3/g$) obtained by dividing the volume of the container (25 $cm^3$) by the mass of the sample. The sample was measured twice, and the average value was used.

(10) Retention Rate of Tocopherol Acetate (%)

2 g of a sample was weighed. While the sample was kneaded, tocopherol acetate (viscosity at 25° C.: 3300 mPa·s) was dropped on the sample little by little. The end point was defined as the amount of the liquid when the liquid eluted on the surface of the sample. The retention rate of tocopherol acetate is represented by the following expression: retention rate of tocopherol acetate (%)=amount of dropped liquid g/2 g of sample×100 The measurement value was defined as the average value of measurement values obtained from two samples.

(11) The Number of Capping to be Occurred 50 tablets after tableting were arbitrarily sampled, and the number of the tablets cracked or partially peeled was counted.

(12) Sticking Occurrence Rate (%)

50 tablets were examined visually, and the number of the tablets having peel-off or damages on the surface was counted. The sticking occurrence rate (%) was defined as the proportion of the number of tablets having sticking.

(13) Weight CV Value 10 tablets after tableting were arbitrarily sampled, and the weights of the samples were measured. From the average value and standard deviation of the measured values, the weight CV value was defined as weight CV value=(standard deviation/average value)×100 [%]. A larger weight CV value causes larger variation in the weight, leading to increase in variation in the content of the drug and reduced yield of products. At a weight CV value of more than 1.0%, practical problems arise.

(14) Scanning Electron Microscope Photograph (Hereinafter, Abbreviated to SEM)

Measurement was performed using an electron microscope (made by JEOL, Ltd., JSM-5510LV type). A sample was mounted on a sample moving stage. According to a gold deposition method (AUTO FINE COATER, made by JEOL, Ltd., JFC-1600 type), the surface of the sample is thinly and uniformly coated with metal particles. Then, the sample moving stage was installed within a sample chamber. The inside of the sample chamber was made to be vacuum. The sample position was irradiated with an electron beam, and an enlarged image of the portion to be observed was output.

(15) Average Polymerization Degree

The average polymerization degree was defined as the value measured by a copper ethylenediamine solution viscosity method described in the Identification Test for Microcrystalline Cellulose (3) of The Japanese Pharmacopoeia, Fourteenth Edition.

(16) L/D of Cellulose Particles Dispersed in Water

The average L/D of cellulose particles dispersed in water was measured as follows. Using a JIS standard sieve (Z8801-1987), an aqueous dispersion liquid of the cellulose was passed through a 75 μm sieve. In the particles remaining on a 38 μm sieve, an optical microscope image of the remaining particles was subjected to an image analysis processing (made by Inter Quest Co., Ltd., apparatus: Hyper700, software: Imagehyper). The L/D of a particle was defined as the ratio of a longer side to a shorter side (longer side/shorter side) of the rectangle having the smallest area among rectangles circumscribed about the particle. The average L/D of the particle was obtained using the average value of L/D obtained from at least 100 particles.

Example 1

A broad leaf tree was subjected to known pulping and bleaching treatments to obtain a pulp (the average width of the cellulose primary particle was approximately 19 μm, and the average thickness of the cellulose primary particle was approximately 3 μm). 4.5 kg of the chipped pulp and 30 L of a 0.2% hydrochloric acid aqueous solution were put into a low speed stirrer (made by Ikebukuro Horo Kogyo Co., Ltd., trade name, 30LGL reactor). While the chipped pulp and the aqueous solution were stirred, hydrolysis was performed at 124° C. for 1 hour to obtain an acid insoluble residue (hereinafter, referred to as a Wet cake). The volume average particle size of the cellulose particle was measured by a laser diffraction/scattering particle size distribution analyzer (made by HORIBA, Ltd., trade name "LA-910") at a refractive index of 1.20. The obtained volume average particle size was 25 µm.

Pure water was introduced into a plastic bucket. While pure water was stirred by a 3-1 motor, the Wet cake was added and mixed. Next, calcium silicate (made by Tokuyama Corporation, product name: Florite R, volume average particle size of 25 µm) was added and mixed. The mass ratio was cellulose/calcium silicate=28.6/71.4 (based on the solid content), and the concentration of the total solid content was approximately 8.5% by mass. The obtained mixture was spray dried (dispersion liquid feed rate of 6 kg/hr, inlet temperature of 180 to 220° C., outlet temperature of 70 to 95° C., number of rotation of an atomizer of 15000 rpm) to obtain Composite Particles A. The physical properties of Composite Particles A are shown in Table 1.

Examples 2 and 3

A broad leaf tree was subjected to known pulping treatment and bleaching treatments to obtain a pulp (the average width of the cellulose primary particle was approximately 19 µm, and the average thickness of the cellulose primary particle was approximately 3 µm). 4.5 kg of the chipped pulp and 30 L of a 0.2% hydrochloric acid aqueous solution were put into a low speed stirrer (made by Ikebukuro Horo Kogyo Co., Ltd., trade name, 30LGL reactor). While the chipped pulp and the aqueous solution were stirred, hydrolysis was performed at 124° C. for 1 hour to obtain an acid insoluble residue (hereinafter, referred to as a Wet cake). The volume average particle size of the cellulose particle was measured by a laser diffraction/scattering particle size distribution analyzer (made by HORIBA, Ltd., trade name "LA-910") at a refractive index of 1.20. The obtained volume average particle size was 25 µm.

Pure water was introduced into a plastic bucket. While pure water was stirred by a 3-1 motor, starch (made by Asahi Kasei Chemicals Corporation, trade name "SWELSTAR" WB-1) was added and mixed. Next, the Wet cake was added and mixed. Next, calcium silicate (made by Tokuyama Corporation, product name: Florite R, volume average particle size of 25 µm) was added and mixed. The mass ratio was starch/cellulose/calcium silicate=10/20/70 (based on the solid content), and the concentration of the total solid content was approximately 8.5% by mass (pH was 10.2). The obtained mixture was spray dried (dispersion liquid feed rate of 6 kg/hr, inlet temperature of 180 to 220° C., outlet temperature of 70 to 95° C., number of rotation of an atomizer of 15000 rpm, 30000 rpm). Thus, Composite Particles B (number of rotation of an atomizer of 15000 rpm) and Composite Particles C (number of rotation of an atomizer of 30000 rpm) were obtained. The physical properties of Composite Particles B and C are shown in Table 1.

Examples 4 and 5

A broad leaf tree was subjected to known pulping and bleaching treatments to obtain a pulp (the average width of the cellulose primary particle was approximately 19 µm, and the average thickness of the cellulose primary particle was approximately 3 µm). 4.5 kg of the chipped pulp and 30 L of a 0.2% hydrochloric acid aqueous solution were put into a low speed stirrer (made by Ikebukuro Horo Kogyo Co., Ltd., trade name, 30LGL reactor). While the chipped pulp and the aqueous solution were stirred, hydrolysis was performed at 124° C. for 1 hour to obtain an acid insoluble residue (hereinafter, referred to as a Wet cake). The volume average particle size of the cellulose particle was measured by a laser diffraction/scattering particle size distribution analyzer (made by HORIBA, Ltd., trade name "LA-910") at a refractive index of 1.20. The obtained volume average particle size was 25 µm.

Pure water was introduced into a plastic bucket. While pure water was stirred by a 3-1 motor, the Wet cake was added and mixed. Next, calcium silicate (made by Tokuyama Corporation, product name: Florite R, volume average particle size of 25 µm) was added and mixed. The mass ratio was cellulose/calcium silicate=20/80 (based on the solid content), and the concentration of the total solid content was approximately 8.5% by mass. The mixture was spray dried (dispersion liquid feed rate of 6 kg/hr, inlet temperature of 180 to 220° C., outlet temperature of 70 to 95° C., number of rotation of an atomizer of 15000 rpm and 30000 rpm). Thus, Composite Particles D (number of rotation of an atomizer of 15000 rpm), and Composite Particles E (number of rotation of an atomizer of 30000 rpm) were obtained. The physical properties of Composite Particles D and E are shown in Table 1.

Examples 6 and 7

Composite particles F (number of rotation of an atomizer of 15000 rpm) and Composite Particles G (number of rotation of an atomizer of 30000 rpm) were obtained in the same manner as in Examples 2 and 3 except that the mass ratio was starch/cellulose/calcium silicate=5/40/55 (based on the solid content). The physical properties of Composite Particles F and G are shown in Table 1.

Examples 8 and 9

Composite Particles H (number of rotation of an atomizer of 15000 rpm) and Composite Particles I (number of rotation of an atomizer of 30000 rpm) were obtained in the same manner as in Examples 2 and 3 except that the mass ratio was starch/cellulose/calcium silicate=7/43/50 (based on the solid content), and the concentration of the total solid content was 9.3% by mass. The physical properties of Composite Particles H and I are shown in Table 1.

Examples 10 and 11

Composite particles J (number of rotation of an atomizer of 15000 rpm) and Composite Particles K (number of rotation of an atomizer of 30000 rpm) were obtained in the same manner as in Examples 4 and 5 except that the mass ratio was cellulose/calcium silicate=60/40 (based on the solid content), and the concentration of the total solid content was 11.7% by mass. The physical properties of Composite Particles J and K are shown in Table 1.

Examples 12 and 13

Composite particles L (number of rotation of an atomizer of 8000 rpm) and Composite Particles M (number of rotation of an atomizer of 30000 rpm) were obtained in the same manner as in Examples 2 and 3 except that the mass ratio was starch/cellulose/calcium silicate=3/60/37 (based on the solid content), the concentration of the total solid content was 11.7% by mass, and the number of rotation of an atomizer was 8000 rpm and 30000 rpm. The physical properties of Composite Particles L and M are shown in Table 1.

Example 14

Composite particles N (number of rotation of an atomizer of 15000 rpm) were obtained in the same manner as in Example 2 except that the mass ratio was starch/cellulose/calcium silicate=2.5/72.5/25 (based on the solid content), and the concentration of the total solid content was 11.7% by mass. The physical properties of Composite Particles N are shown in Table 1.

Example 15

Composite particles O (number of rotation of an atomizer of 30000 rpm) were obtained in the same manner as in Example 5 except that the mass ratio was cellulose/light anhydrous silicic acid=50/50 (based on the solid content), and the concentration of the total solid content was 4% by mass. The physical properties of Composite Particles O are shown in Table 1.

Example 16

Composite particles P (number of rotation of an atomizer of 15000 rpm) were obtained in the same manner as in Example 4 except that the mass ratio was cellulose/magnesium aluminometasilicate=30/70 (based on the solid content), and the concentration of the total solid content was 5% by mass. The physical properties of Composite Particles P are shown in Table 1.

Example 17

Composite particles Q (number of rotation of an atomizer of 15000 rpm) were obtained in the same manner as in Example 4 except that the mass ratio was cellulose/magnesium silicate hydrate=50/50 (based on the solid content), and the concentration of the total solid content was 5% by mass. The physical properties of Composite Particles Q are shown in Table 1.

TABLE 1

| | | Cellulose average width [μm] | Cellulose average thickness [μm] | Cellulose volume average particle size [μm] | Inorganic compound volume average particle size [μm] | Cellulose parts by mass | Inorganic compound parts by mass | Kind of inorganic compound |
|---|---|---|---|---|---|---|---|---|
| Example 1 | A | 19 | 3 | 25 | 25 | 28.6 | 71.4 | Calcium silicate Ca |
| Example 2 | B | 19 | 3 | 25 | 25 | 20 | 70 | Calcium silicate Ca |
| Example 3 | C | 19 | 3 | 25 | 25 | 20 | 70 | Calcium silicate Ca |
| Example 4 | D | 19 | 3 | 25 | 25 | 20 | 80 | Calcium silicate ca |
| Example 5 | E | 19 | 3 | 25 | 25 | 20 | 80 | Calcium silicate Ca |
| Example 6 | F | 19 | 3 | 25 | 25 | 40 | 55 | Calcium silicate Ca |
| Example 7 | G | 19 | 3 | 25 | 25 | 40 | 55 | Calcium silicate Ca |
| Example 8 | H | 19 | 3 | 25 | 25 | 43 | 50 | Calcium silicate Ca |
| Example 9 | I | 19 | 3 | 25 | 25 | 43 | 50 | Calcium silicate Ca |
| Example 10 | J | 19 | 3 | 25 | 25 | 60 | 40 | Calcium silicate Ca |
| Example 11 | K | 19 | 3 | 25 | 25 | 60 | 40 | Calcium silicate Ca |
| Example 12 | L | 19 | 3 | 25 | 25 | 60 | 37 | Calcium silicate Ca |
| Example 13 | M | 19 | 3 | 25 | 25 | 60 | 37 | Calcium silicate Ca |
| Example 14 | N | 19 | 3 | 25 | 25 | 72.5 | 25 | Calcium silicate Ca |
| Example 15 | O | 19 | 3 | 20 | 0.016 | 50 | 50 | Light anhydrous silicic acid |
| Example 16 | P | 19 | 3 | 25 | 12 | 30 | 70 | Magnesium aluminometasilicate |
| Example 17 | Q | 19 | 3 | 50 | 0.07 | 50 | 50 | Magnesium silicate hydrate Mg |

| | Starch parts by mass | Apparent specific volume [cm³/g] | Repose angle [°] | Pore volume [cm³/g] | Porosity [%] | Weight average particle size [μm] | Retention rate of tocopherol acetate [%] | Hardness of tablet [N] |
|---|---|---|---|---|---|---|---|---|
| Example 1 | — | 10.8 | 35 | 2.71 | 33.1 | 48 | 860 | 240 |
| Example 2 | 10 | 10.4 | 34.5 | 2.70 | 32.4 | 38 | 830 | 233 |
| Example 3 | 10 | 10.7 | 37.5 | 2.81 | 33.1 | 55 | 860 | 244 |
| Example 4 | — | 11.5 | 35 | 3.15 | 35.5 | 31 | 915 | 325 |
| Example 5 | — | 11.6 | 36.5 | 3.15 | 35.5 | 32 | 875 | 312 |
| Example 6 | 5 | 8.7 | 32 | 1.97 | 27.4 | 80 | 703 | 243 |
| Example 7 | 5 | 8.8 | 34 | 2.09 | 28.2 | 60 | 738 | 261 |
| Example 8 | 7 | 9.4 | 30 | 2.32 | 29.8 | 90 | 725 | 264 |
| Example 9 | 7 | 8.7 | 33 | 2.05 | 28.0 | 70 | 760 | 240 |
| Example 10 | — | 8.2 | 35 | 1.84 | 26.5 | 65 | 575 | 239 |
| Example 11 | — | 7.7 | 39 | 1.63 | 25.0 | 50 | 520 | 220 |
| Example 12 | 3 | 7.1 | 35 | 1.43 | 23.8 | 210 | 590 | 190 |
| Example 13 | 3 | 7.2 | 35.5 | 1.48 | 24.1 | 61 | 530 | 200 |
| Example 14 | 2.5 | 7.1 | 38.5 | 1.44 | 23.9 | 49 | 485 | 236 |
| Example 15 | — | 12.5 | 41 | 1.50 | 25.1 | 29 | 500 | 150 |

TABLE 1-continued

| | | | | | | | | |
|---|---|---|---|---|---|---|---|---|
| Example 16 | — | 10.5 | 37 | 1.55 | 24.9 | 40 | 510 | 170 |
| Example 17 | — | 11.6 | 38 | 1.21 | 20.2 | 38 | 450 | 148 |

Reference Example 1

100 g of pure water was introduced into a stainless steel jug. While pure water was stirred by a 3-1 motor, calcium silicate (made by Tokuyama Corporation, product name: Florite R, volume average particle size of 25 to 30 μm) was added little by little with a dispensing spoon and stirred. When the amount of calcium silicate added reached 10.7 g, stirring became impossible.

Reference Example 2

Pure water was introduced into a stainless steel jug. While pure water was stirred by a 3-1 motor, the Wet cake obtained in Example 1 was added and mixed. Next, while $SiO_2$ (trade name: Aerosil 200, made by Nippon Aerosil Co., Ltd., volume average particle size of 0.016 μm) was added little by little with a dispensing spoon, the materials were stirred and mixed. The mass ratio was cellulose/light anhydrous silicic acid=29.3/70.7 (based on the solid content), and the concentration of the total solid content was 8.5% by mass (pH was 10.2). The obtained product was gluey, and could not be spray dried.

Reference Example 3

Pure water was introduced into a stainless steel jug. While pure water was stirred by a 3-1 motor, the Wet cake obtained in Example 1 was added and mixed. Next, magnesium aluminometasilicate (trade name: Neusilin, made by Fuji Chemical Industry Co., Ltd.) was mixed. The mass ratio was cellulose/magnesium aluminometasilicate=31.0/69.0 (based on the solid content), and the concentration of the total solid content was 11.7% by mass (pH was 10.2). The obtained product was creamy, and could not be spray dried.

Comparative Example 1

The physical properties of calcium silicate (made by Tokuyama Corporation, product name: Florite R, volume average particle size of 25 μm) are shown in Table 2.

Comparative Example 2

Composite particles R were obtained in the same manner as in Example 4 except that the mass ratio was starch/cellulose/calcium silicate=2.5/72.5/25 (based on the solid content), and the concentration of the total solid content was 11.7% by mass. The physical properties of Composite Particles R are shown in Table 2.

Comparative Example 3

2 kg of a chipped commercially available dissolved pulp (acicular tree pulp, average width of the cellulose primary particle was approximately 39 μm, average thickness of the cellulose primary particle was approximately 8 μm) and 30 L of a 0.4% hydrochloric acid aqueous solution were put into a low speed stirrer (made by Ikebukuro Horo Kogyo Co., Ltd., trade name, 30LGL reactor). While the chipped pulp and the aqueous solution were stirred, hydrolysis was performed at 116° C. for 1 hour to obtain an acid insoluble residue (the volume average particle size of the cellulose dispersed particle was 51 μm, and L/D was 3.4). The obtained acid insoluble residue and silicon dioxide (made by Tokuyama Corporation, trade name, FINESEAL, volume average particle size of 5 μm) as a water insoluble inorganic compound were introduced into a 90 L plastic bucket at an amount ratio of 30/70 (based on the solid content). Pure water was added such that the concentration of the total solid content became 20% by weight. While the materials were stirred by a 3-1 motor, the materials were neutralized with aqueous ammonia (pH after neutralization was 7.5 to 8.0). The obtained product was spray dried (dispersion liquid feed rate of 6 kg/hr, inlet temperature of 180 to 220° C., outlet temperature of 50 to 70° C., number of rotation of an atomizer of 30000 rpm) to obtain Composite Particles S (corresponding to Example 2 in Patent Literature 3). The physical properties of Composite Particles S are shown in Table 2.

Comparative Example 4

2 kg of a chipped commercially available pulp (acicular tree pulp, average width of the cellulose primary particle was approximately 39 μm, average thickness of the cellulose primary particle was approximately 8 μm) and 30 L of a 0.2% hydrochloric acid aqueous solution were put into a low speed stirrer (made by Ikebukuro Horo Kogyo Co., Ltd., trade name, 30LGL reactor). While the chipped pulp and the aqueous solution were stirred, hydrolysis was performed at 116° C. for 1 hour to obtain an acid insoluble residue (the volume average particle size of the cellulose dispersed particle was 72 μm, and L/D was 4.0). The acid insoluble residue (solid content) and talc (made by Wako Pure Chemical Industries, Ltd., prepared so as to have a volume average particle size of 5 μm) were introduced into a 90 L plastic bucket at an amount ratio of 98/2 (based on the solid content). Pure water was added such that the concentration of the total solid content became 10% by weight. While the materials were stirred by a 3-1 motor, the materials were neutralized with aqueous ammonia (pH after neutralization was 7.5 to 8.0). The obtained product was spray dried in the same manner as that in Comparative Example 3 to obtain Composite Particles T (corresponding to Example 6 in Patent Literature 3). The physical properties of Composite Particles T are shown in Table 2.

Comparative Example 5

Ceolus PH-101 (made by Asahi Kasei Chemicals Corporation) was used as a microcrystalline cellulose. The cellulose and calcium silicate at a mass ratio of cellulose/calcium silicate=28.6/71.4 were sufficiently mixed in a plastic bag for 3 minutes to obtain Mixture U of cellulose/calcium silicate (the mixture having the largest amount of silicic acid to be blended which is described in Patent Literature 4). The physical properties of Mixture U are shown in Table 2.

Comparative Example 6

Ceolus PH-101 (made by Asahi Kasei Chemicals Corporation) was used as a microcrystalline cellulose. The cellulose and calcium silicate at a mass ratio of cellulose/calcium silicate=71.4/28.6 were sufficiently mixed in a plastic bag for 3 minutes to obtain Mixture V of cellulose/calcium silicate (the mixture having the smallest amount of silicic acid to be blended which is described in Patent Literature 4). The physical properties of Mixture V are shown in Table 2.

TABLE 2

| | | Cellulose average width [μm] | Cellulose average thickness [μm] | Cellulose particle size [μm] | Inorganic compound particle size [μm] | Cellulose parts by mass | Inorganic compound parts by mass | Kind of inorganic compound |
|---|---|---|---|---|---|---|---|---|
| Comparative Example 1 | — | — | — | — | 25 | — | 100 | Calcium silicate Ca |
| Comparative Example 2 | R | 19 | 3 | 22-27 | 25 | 72.5 | 25 | Calcium silicate Ca |
| Comparative Example 3 | S | 39 | 8 | 51 | 5 | 30 | 70 | Silicon dioxide |
| Comparative Example 4 | T | 39 | 8 | 72 | 5 | 98 | 2 | Talc |
| Comparative Example 5 | U | 39 | 8 | 38 | 25 | 28.6 | 71.4 | Calcium silicate Ca |
| Comparative Example 6 | V | 39 | 8 | 38 | 25 | 71.4 | 28.6 | Calcium silicate Ca |

| | Starch parts by mass | Apparent specific volume [cm$^3$/g] | Repose angle [°] | Pore volume [cm$^3$/g] | Porosity [%] | Average particle size [μm] | Retention rate of tocopherol acetate [%] | Hardness of tablet [N] |
|---|---|---|---|---|---|---|---|---|
| Comparative Example 1 | — | 13.7 | 40 | 3.95 | 41.0 | 56 | 885 | 348 |
| Comparative Example 2 | 2.5 | 6.9 | 40.5 | 1.37 | 23.3 | 50 | 440 | 215 |
| Comparative Example 3 | — | 5.1 | 32 | 1.25 | 22.1 | 52 | 400 | 45 |
| Comparative Example 4 | — | 6 | 45 | 0.29 | 17.2 | 45 | 204 | 110 |
| Comparative Example 5 | — | 11 | 42 | 1.88 | 27.1 | 29 | 687 | 265 |
| Comparative Example 6 | — | 7.4 | 38 | 1.00 | 20.4 | 39 | 390 | 145 |

<SEM Photograph>

Using a "JSM-5510LV type" electron microscope made by JEOL, Ltd., Composite Particles B, D, G, I, K, and M were observed by SEM.

Figure 2:
FIG. 2 is an enlarged SEM photograph at a magnification of 500 times of Composite Particles D according to Example 4.
Figure 3:
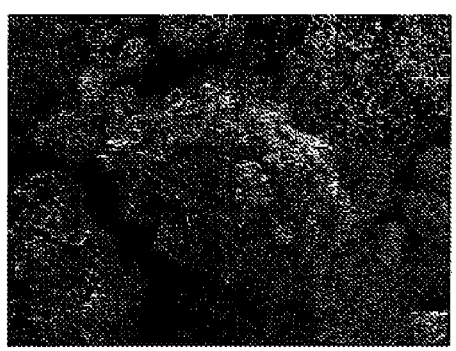
FIG. 3 is an enlarged SEM photograph at a magnification of 500 times of Composite Particles G according to Example 7.
Figure 4:
FIG. 4 is an enlarged SEM photograph at a magnification of 500 times of Composite Particles I according to Example 9.
Figure 5:
FIG. 5 is an enlarged SEM photograph at a magnification of 200 times of a dried product of a cellulose WET cake.
Figure 6:
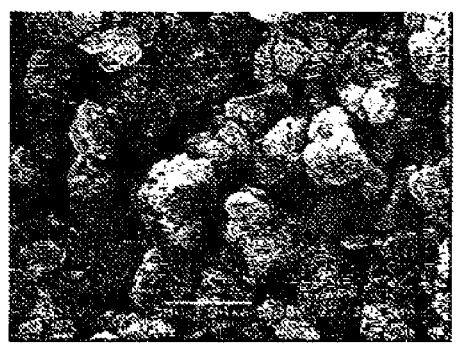
FIG. 6 is an enlarged SEM photograph at a magnification of 500 times of calcium silicate according to Reference Example 2.

It is found that the particle has relatively few irregularities on the surface, and has a shape close to a sphere in Composite Particles B in Example 2 (see FIG. 1), Composite Particles D in Example 4 (see FIG. 2), Composite Particles G in Example 7 (see FIG. 3), and Composite Particles I in Example 9 (see FIG. 4). It is also found that the cellulose WET cake (see FIG. 5) and calcium silicate in Reference Example 2 (see FIG. 6) are formed into a composite product which has gaps. The gaps can provide a molded article having high liquid retention rate and hardness.

Figure 7:
FIG. 7 is an enlarged SEM photograph at a magnification of 500 times of Composite Particles K according to Example 11.
Figure 8:
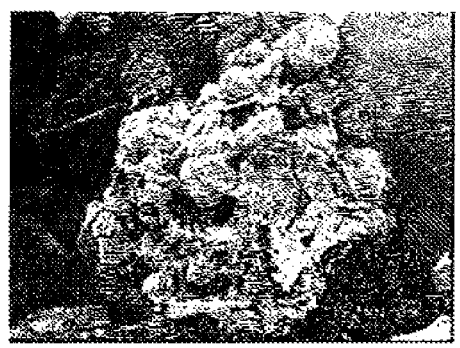
FIG. 8 is an enlarged SEM photograph at a magnification of 500 times of Composite Particles M according to Example 13.

Meanwhile, the particle has irregularities on the surface in Composite Particles K in Example 11 (FIG. 7) and Composite Particles M in Example 13 (see FIG. 8).

<Evaluation of Prevention of Sticking>

Ibuprofen is a representative example of a drug easy to stick. Using ibuprofen, comparison was made about the sticking-preventing effect. Granulated granules having ibuprofen blended were produced by the following method.

In the total amount of ingredients of 1000 g, 45% of ibuprofen (made by API Corporation), 38% of lactose hydrate (trade name: lactose 200M, made by DMV International), and 17% of corn starch (GRDE: ST-C, made by NIPPON STARCH CHEMICAL CO., LTD.) were weighed and mixed in a polyethylene bag for 3 minutes. Then, the mixture was placed in a vertical granulator (made by Powrex Corporation, FM-VG-10P type) and mixed (blade at 200 rpm, chopper at 2100 rpm). 200 g of a hydroxypropyl cellulose (trade name: HPC-L, made by NIPPON SODA CO., LTD.) 6% solution was poured over 30 seconds. Further, the ingredients were mixed (granulated) for 3 minutes, and taken out from the granulator. Next, the mixture was dried using a MULTIPLEX (made by Powrex Corporation, MP-01 type). The drying was completed when the temperature of exhaust air reached 40° C. Then, a granulated product was extracted. The granulated product was sieved with a sieve having an opening of 710 μm, and used as a test sample (hereinafter, referred to as granulated granules).

Example 18

88% by mass of the granulated granules, 2% by mass of croscarmellose sodium (made by NICHIRIN CHEMICAL INDUSTRIES, LTD.), "KICCOLATE" ND-2HS), and 10% by mass of Composite Particles C of Example 3 were mixed in a polyethylene bag for 3 minutes. Next, based on the total weight of the mixed powder, 0.5% by mass of magnesium stearate (made by TAIHEI CHEMICAL INDUSTRIAL CO., LTD.) was added, and mixed slowly for 30 seconds. Using a rotary tableting machine (made by Kikusui Seisakusho Ltd., CLEANPRESS CORRECT 12HUK), the mixed powder was tableted with a punch having a diameter of 0.8 cm and 12 R on the condition of the number of rotation of the turn table of 54 rpm, a compression force of 5 to 15 kN, and open feed. Thus, a tablet having a weight of 180 mg was produced. The physical properties of the tablet are shown in Table 3.

Example 19

The operation was performed in the same manner as that in Example 18 except that Composite Particles C used in Example 18 were replaced by Composite Particles H of Example 8. The physical properties of the tablet are shown in Table 3.

Comparative Example 7

The operation was performed in the same manner as that in Example 18 except that Composite Particles C used in Example 18 were replaced by light anhydrous silicic acid (made by Nippon Aerosil Co., Ltd., Aerosil 200). The physical properties of the tablet are shown in Table 3.

Comparative Example 8

The operation was performed in the same manner as that in Example 18 except that Composite Particles C used in Example 18 were replaced by Composite Particles S of Comparative Example 3. The physical properties of the tablet are shown in Table 3.

Comparative Example 9

The operation was performed in the same manner as that in Example 18 except that Composite Particles C used in Example 18 were replaced by Composite Particles T of Comparative Example 4. The physical properties of the tablet are shown in Table 3.

Comparative Example 10

The operation was performed in the same manner as that in Example 18 except that Composite Particles C used in Example 18 were replaced by Mixture U of Comparative Example 5. The physical properties of the tablet are shown in Table 3.

Comparative Example 11

The operation was performed in the same manner as that in Example 18 except that Composite Particles C used in Example 18 were replaced by Mixture V of Comparative Example 6. The physical properties of the tablet are shown in Table 3.

In Examples 18 and 19, tablets having a practical hardness of 50 N or more, the weight CV value of 1.0% or less, and no tableting problems (sticking, capping) were obtained. Meanwhile, in Comparative Example 7, tableting problems (no sticking, but two cappings) were occurred. The weight CV value was more than 1.0%. Accordingly, the tablet in Comparative Example 7 is not suitable for practical use. In Comparative Examples 8 to 11, the weight CV value was more than 1.0%, and tableting problems (sticking, capping) were remarkable. Accordingly, the tablets in Comparative Examples 8 to 11 are not suitable for practical use.

In Comparative Example 9, a practical hardness of 50 N or more was obtained at the compression force of 15 kN while the friability was 0.8% and did not satisfy the practical level of 0.5% or less.

The disintegrating time of the tablet was measured in the respective tablets, but no remarkable difference was found among the tablets.

<Method for Producing Emulsion Solution>

360 g of Riken tocopherol acetate (Riken Vitamin Co., Ltd.) as an liquid active ingredient, Tween 80 (Wako Pure Chemical Industries, Ltd.), and 1000 g of pure water were weighed, and stirred and mixed with a TK homomixer (PRIMIX Corporation, MARK2 2.5 type) at 10000 rpm for 15 minutes to produce an emulsified solution.

Example 20

360 g of Composite Particles C of Example 3 was put into a vertical granulator (made by Powrex Corporation, FM-VG-10P). While Composite Particles C were mixed on the condition of a blade at 200 rpm and a chopper at 2100 rpm, 360 g of the emulsified solution produced above was poured in 30 seconds. The obtained mixture was granulated for 6 minutes, and discharged. Next, the granulated product was dried with an oven (made by Tabai Espec Corp., ESPEC Oven PV-211), and passed through a sieve having an opening of 710 μm (made by Iida Seisakusho K.K., sieve for a test) to obtain a dried product. The dried product was used as a test sample (hereinafter, referred to as VE granules). The repose angle of the VE granules was 35° and good.

35% by mass of the VE granules, 45% by mass of a microcrystalline cellulose (made by Asahi Kasei Chemicals Corporation, UF-711), 18% by mass of anhydrous dibasic calcium phosphate (made by Fuji Chemical Industry Co., Ltd., Fujicalin), and 2% by mass of croscarmellose sodium (made by NICHIRIN CHEMICAL INDUSTRIES, LTD,

TABLE 3

| | | Hardness [N] | | | Mass CV [%] | | | Friability [%] | | | Sticking occurrence rate [%] | Number of cappings occurred |
|---|---|---|---|---|---|---|---|---|---|---|---|---|
| | | | | | | | | Compression force [kN] | | | | |
| | Items | 5 | 10 | 15 | 5 | 10 | 15 | 5 | 10 | 15 | 15 | 15 |
| Example 18 | Composite particles C | 59 | 85 | 102 | 0.5 | 0.6 | 0.5 | 0.45 | 0.15 | 0.11 | 0 | None |
| Example 19 | Composite particles H | 70 | 90 | 79 | 0.9 | 0.5 | 0.9 | 0.16 | 0.08 | 0.17 | 0 | None |
| Comparative Example 7 | Light anhydrous silicic acid | 30 | 53 | 38 | 2.2 | 2.1 | 1.6 | 0.39 | 0.43 | 2.85 | 0 | 2 |
| Comparative Example 8 | Composite particles S | 20 | 35 | 40 | 1.9 | 2.3 | 1.5 | 2.50 | 1.90 | 1.20 | 5 | 25 |
| Comparative Example 9 | Composite particles T | 20 | 48 | 60 | 2.8 | 1.8 | 3.4 | 2.40 | 1.00 | 0.80 | 20 | 5 |
| Comparative Example 10 | Mixture U | 26 | 40 | 30 | 1.5 | 1.4 | 1.9 | 1.00 | 0.90 | 0.80 | 10 | 25 |
| Comparative Example 11 | Mixture V | 20 | 37 | 43 | 1.8 | 1.6 | 2.1 | 1.8 | 1.20 | 0.70 | 50 | 40 |

"KICCOLATE" ND-2HS) were mixed in a polyethylene bag for 3 minutes. Next, based on the total weight of the mixed powder, 2.0% by mass of magnesium stearate (made by TAIHEI CHEMICAL INDUSTRIAL CO., LTD.) was added, and further mixed slowly for 30 seconds. Using a rotary tableting machine (made by Kikusui Seisakusho Ltd., LIBRA2), the mixed powder was tableted using a punch having a diameter of 0.8 cm and 12 R on the condition of the number of rotation of the turn table of 30 rpm, the compression force of 2 to 7 kN, and open feed to produce a tablet having a weight of 200 mg. The physical properties of the tablet are shown in Table 4.

Comparative Example 12

The operation was performed in the same manner as in Example 20 except that Composite Particles C were replaced by calcium silicate (made by Tokuyama Corporation, product name: Florite Grade®, volume average particle size (which was measured at the state of aggregated particles) of 25 to 30 μm). The physical properties of the tablet are shown in Table 4. The repose angle of the VE granules was 41°. Fluidity was inferior to that in the case where Composite Particles C were used.

Comparative Example 13

The operation was performed in the same manner as in Example 20 except that Composite Particles C were replaced by Composite Particles S. The physical properties of the tablet are shown in Table 4.

Comparative Example 14

The operation was performed in the same manner as in Example 20 except that Composite Particles C were replaced by Mixture U. The physical properties of the tablet are shown in Table 4.

TABLE 4

| | Items | Sticking occurrence rate [%] Compression force [kN] | | | | | |
|---|---|---|---|---|---|---|---|
| | | 2 | 3 | 4 | 5 | 6 | 7 |
| Example 20 | Composite particles C | | | 0 | | 0 | 0 |
| Comparative Example 12 | Calcium silicate | 31.0 | 11.3 | | | 75.0 | |
| Comparative Example 13 | Composite particles S | | | Powder cannot be obtained | | | |
| Comparative Example 14 | Mixture U | | | Powder cannot be obtained | | | |

In Example 20, a tablet having a practical hardness of 50 N or more, a weight CV value of 1.0% or less, and no tableting problems (sticking, capping) were obtained. Meanwhile, in Comparative Example 12, the sticking occurrence rate was not 0 at all of the compression forces. Accordingly, the tablet is not suitable for practical use. In Comparative Examples 13 and 14, the retention rate of tocopherol acetate was low, and powder could not be obtained.

INDUSTRIAL APPLICABILITY

The composite particles according to the present invention have extremely high compactibility and fluidity. For this reason, the composite particles according to the present invention have high uniformity of mixing with the active ingredients when the composite particles according to the present invention are used as an excipient mainly in the pharmaceutical field in production of a molded article containing a variety of active ingredients. Moreover, the composite particles according to the present invention can keep the compactibility and fluidity of the particles even after retention of the liquid to prevent tableting problems. In addition, the weight of the molded article according to the present invention is hardly fluctuated. The molded article according to the present invention has high uniformity of the active ingredients contained, high sufficient hardness, and low friability.

The invention claimed is:

1. Composite particles comprising a cellulose and an inorganic compound, wherein an apparent specific volume of the composite particles is 7 to 13 cm$^3$/g, and a volume average particle size of the cellulose as a water-dispersed cellulose is 10 to 40 μm.

2. The composite particles according to claim 1, comprising 10 to 60 parts by mass of the cellulose and 40 to 90 parts by mass of the inorganic compound.

3. The composite particles according to claim 1, wherein the inorganic compound is at least one selected from the group consisting of silicon dioxide hydrate, light anhydrous silicic acid, synthetic aluminum silicate, magnesium hydroxide-aluminum hydroxide co-precipitate, magnesium aluminometasilicate, magnesium aluminosilicate, calcium silicate, non-crystalline silicon oxide hydrate, magnesium silicate, and magnesium silicate hydrate.

4. The composite particles according to claim 1, wherein the inorganic compound is calcium silicate.

5. The composite particles according to claim 1, wherein a pore size of the composite particles is 0.003 to 1 μm, and a pore volume of the composite particles is 1.9 to 3.9 cm$^3$/g.

6. The composite particles according to claim 1, wherein a retention rate for the composite particles of tocopherol acetate is 500 to 1000%.

7. The composite particles according to claim 1, wherein a weight average particle size of the composite particles is 30 to 250 μm.

8. The composite particles according to claim 1, further comprising starch.

9. A molded article comprising the composite particles according to claim 1 and an active ingredient.

10. The molded article according to claim 9, wherein the active ingredient is an ingredient for a medicament or an ingredient for health food.

11. A molded article comprising composite particles comprising a cellulose and an inorganic compound, wherein an apparent specific volume of the composite particles is 7 to 13 cm$^3$/g, and a volume average particle size of the cellulose as a water-dispersed cellulose is 10 to 40 μm, and an active ingredient, wherein the active ingredient is a liquid having a viscosity at 25° C. of 3 to 10000 mPa·s, and the molded article contains 105 to 250 mg of the active ingredient per 500 mg of one molded article.

12. The molded article according to claim 11, wherein the active liquid ingredient is tocopherol acetate.

* * * * *